(12) United States Patent
Struck et al.

(10) Patent No.: US 12,409,045 B2
(45) Date of Patent: Sep. 9, 2025

(54) 3D PRINTED CERVICAL STANDALONE IMPLANT

(71) Applicant: VB Spine US Opco LLC, Leesburg, VA (US)

(72) Inventors: Jared Gordon Struck, Sterling, VA (US); Dane Matthew Johannessen, Reston, VA (US); Robert Clint Boyd, Leesburg, VA (US); Bryan D. Milz, Florida, NY (US); Choll Kim, San Diego, CA (US); Alex Mohit, Puyallup, WA (US); Yashar Javidan, Sacramento, CA (US)

(73) Assignee: VB Spine US Opco LLC, Wilmington, DE (US)

( * ) Notice: Subject to any disclaimer, the term of this patent is extended or adjusted under 35 U.S.C. 154(b) by 352 days.

(21) Appl. No.: 18/071,137

(22) Filed: Nov. 29, 2022

(65) Prior Publication Data
US 2023/0103107 A1 Mar. 30, 2023

Related U.S. Application Data

(63) Continuation of application No. 17/019,912, filed on Sep. 14, 2020, now Pat. No. 11,534,307.
(Continued)

(51) Int. Cl.
*A61F 2/44* (2006.01)
*A61F 2/30* (2006.01)
*A61F 2/46* (2006.01)

(52) U.S. Cl.
CPC .......... *A61F 2/442* (2013.01); *A61F 2/30771* (2013.01); *A61F 2/3094* (2013.01);
(Continued)

(58) Field of Classification Search
CPC .... A61F 2/442; A61F 2/4611; A61F 2/30771; A61F 2/3094; A61F 2002/30395; A61F 2002/30841; A61F 2002/30985
(Continued)

(56) References Cited

U.S. PATENT DOCUMENTS 4,798,610 A 1/1989 Averill et al.
5,286,573 A 2/1994 Prinz et al.
(Continued)

FOREIGN PATENT DOCUMENTS

DE 102008024281 A1 12/2009
DE 102008024288 A1 12/2009
(Continued)

OTHER PUBLICATIONS

International Search Report and Written Opinion issued in corresponding PCT Appln. No. PCT/US2018/041238.
(Continued)

*Primary Examiner* — Jessica Weiss
(74) *Attorney, Agent, or Firm* — Lerner David LLP

(57) ABSTRACT

In one embodiment, an intervertebral implant includes a body and a locking element. The body includes a leading surface and a trailing surface opposite the leading surface. The body also includes first and second bone fastener passageways through the implant body and a cavity in between the first and second passageways. The cavity includes a trailing wall that separates the cavity from the trailing surface. The locking element is disposed in the cavity such that part of the locking element is visible through an access opening in the trailing wall so that the locking element may be rotated from outside of the implant. In a first rotational position, a first part of the locking element is located within one of the first and second passageways and
(Continued)

in a second rotational position, the first part of the locking element is inside the body covered by the trailing wall.

20 Claims, 24 Drawing Sheets

Related U.S. Application Data

(60) Provisional application No. 62/900,937, filed on Sep. 16, 2019.

(52) U.S. Cl.
CPC ... *A61F 2/4611* (2013.01); *A61F 2002/30395* (2013.01); *A61F 2002/30841* (2013.01); *A61F 2002/30985* (2013.01)

(58) Field of Classification Search
USPC .......................................... 623/17.11–17.16
See application file for complete search history.

(56) References Cited

U.S. PATENT DOCUMENTS

| | | |
|---|---|---|
| 5,411,523 A | 5/1995 | Goble |
| 5,466,237 A | 11/1995 | Byrd, III et al. |
| 5,474,555 A | 12/1995 | Puno et al. |
| 5,534,031 A | 7/1996 | Matsuzaki et al. |
| 5,595,703 A | 1/1997 | Swaelens et al. |
| 5,645,084 A | 7/1997 | McKay |
| 5,669,909 A | 9/1997 | Zdeblick et al. |
| 5,733,286 A | 3/1998 | Errico et al. |
| 5,768,134 A | 6/1998 | Swaelens et al. |
| 5,776,196 A * | 7/1998 | Matsuzaki .............. A61L 27/06 606/247 |
| 5,782,919 A | 7/1998 | Zdeblick et al. |
| 5,943,235 A | 8/1999 | Earl et al. |
| 5,968,098 A | 10/1999 | Winslow |
| 5,984,967 A | 11/1999 | Zdeblick et al. |
| 6,010,502 A | 1/2000 | Bagby |
| 6,039,762 A | 3/2000 | McKay |
| 6,086,614 A | 7/2000 | Mumme |
| 6,117,135 A * | 9/2000 | Schlapfer ............ A61B 17/7044 623/17.11 |
| 6,193,721 B1 | 2/2001 | Michelson |
| 6,206,922 B1 | 3/2001 | Zdeblick et al. |
| 6,235,033 B1 | 5/2001 | Brace et al. |
| 6,245,072 B1 | 6/2001 | Zdeblick et al. |
| 6,258,089 B1 | 7/2001 | Campbell et al. |
| 6,306,139 B1 | 10/2001 | Fuentes |
| 6,331,179 B1 | 12/2001 | Freid et al. |
| 6,375,655 B1 | 4/2002 | Zdeblick et al. |
| 6,391,058 B1 | 5/2002 | Kuslich et al. |
| 6,432,107 B1 | 8/2002 | Ferree |
| 6,447,512 B1 | 9/2002 | Landry et al. |
| 6,471,724 B2 | 10/2002 | Zdeblick et al. |
| 6,485,517 B1 | 11/2002 | Michelson |
| 6,520,996 B1 | 2/2003 | Manasas et al. |
| 6,524,312 B2 | 2/2003 | Landry et al. |
| 6,530,955 B2 | 3/2003 | Boyle et al. |
| 6,530,956 B1 | 3/2003 | Mansmann |
| 6,558,423 B1 * | 5/2003 | Michelson .......... A61B 17/8875 623/17.11 |
| 6,595,995 B2 | 7/2003 | Zdeblick et al. |
| 6,613,091 B1 | 9/2003 | Zdeblick et al. |
| 6,645,206 B1 | 11/2003 | Zdeblick et al. |
| 6,645,227 B2 | 11/2003 | Fallin et al. |
| 6,695,845 B2 | 2/2004 | Dixon et al. |
| 6,695,851 B2 | 2/2004 | Zdeblick et al. |
| 6,716,247 B2 | 4/2004 | Michelson |
| 6,730,127 B2 | 5/2004 | Michelson |
| 6,736,820 B2 | 5/2004 | Biedermann et al. |
| 6,749,636 B2 | 6/2004 | Michelson |
| 6,758,849 B1 | 7/2004 | Michelson |
| 6,884,242 B2 | 4/2005 | LeHuec et al. |
| 6,890,355 B2 | 5/2005 | Michelson |
| 6,902,565 B2 | 6/2005 | Berger et al. |
| 6,964,664 B2 | 11/2005 | Freid et al. |
| 6,972,019 B2 | 12/2005 | Michelson |
| 6,989,031 B2 | 1/2006 | Michelson |
| 7,033,394 B2 | 4/2006 | Michelson |
| 7,041,135 B2 | 5/2006 | Michelson |
| 7,087,057 B2 | 8/2006 | Konieczynski et al. |
| 7,131,974 B2 | 11/2006 | Keyer et al. |
| 7,163,561 B2 | 1/2007 | Michelson |
| 7,175,624 B2 | 2/2007 | Konieczynski et al. |
| 7,238,186 B2 | 7/2007 | Zdeblick et al. |
| 7,238,206 B2 | 7/2007 | Lange et al. |
| 7,288,094 B2 | 10/2007 | Lindemann et al. |
| 7,294,134 B2 | 11/2007 | Weber |
| 7,300,440 B2 | 11/2007 | Zdeblick et al. |
| 7,306,605 B2 | 12/2007 | Ross |
| 7,309,340 B2 | 12/2007 | Fallin et al. |
| 7,318,825 B2 | 1/2008 | Butler et al. |
| 7,435,262 B2 | 10/2008 | Michelson |
| 7,442,209 B2 | 10/2008 | Michelson |
| 7,455,692 B2 | 11/2008 | Michelson |
| 7,509,183 B2 | 3/2009 | Lin et al. |
| 7,527,629 B2 | 5/2009 | Link et al. |
| 7,527,639 B2 | 5/2009 | Orbay et al. |
| 7,537,663 B2 | 5/2009 | Phelps et al. |
| 7,537,664 B2 | 5/2009 | O'Neill et al. |
| 7,540,882 B2 | 6/2009 | Michelson |
| 7,608,080 B2 | 10/2009 | Shipp et al. |
| 7,611,536 B2 | 11/2009 | Michelson |
| 7,618,418 B2 | 11/2009 | Malandain |
| 7,621,958 B2 | 11/2009 | Zdeblick et al. |
| 7,635,366 B2 | 12/2009 | Abdou |
| 7,637,951 B2 | 12/2009 | Michelson |
| 7,637,954 B2 | 12/2009 | Michelson |
| 7,665,979 B2 | 2/2010 | Heugel |
| 7,666,185 B2 | 2/2010 | Ryan et al. |
| 7,674,279 B2 | 3/2010 | Johnson |
| 7,736,380 B2 | 6/2010 | Johnston et al. |
| 7,794,502 B2 | 9/2010 | Michelson |
| 7,811,292 B2 | 10/2010 | Lo et al. |
| 7,875,062 B2 | 1/2011 | Lindemann et al. |
| 7,901,458 B2 | 3/2011 | DeRidder et al. |
| 7,905,886 B1 | 3/2011 | Curran et al. |
| 7,909,872 B2 | 3/2011 | Pipnick et al. |
| 7,914,561 B2 | 3/2011 | Konieczynski et al. |
| 7,935,137 B2 | 5/2011 | Gorhan et al. |
| 7,935,149 B2 | 5/2011 | Michelson |
| 7,963,982 B2 | 6/2011 | Kirschman |
| 7,981,142 B2 | 7/2011 | Konieczynski et al. |
| 7,985,258 B2 | 7/2011 | Zdeblick et al. |
| 7,988,714 B2 | 8/2011 | Puekert et al. |
| 7,998,215 B2 | 8/2011 | Frey et al. |
| 8,043,343 B2 | 10/2011 | Miller et al. |
| 8,062,342 B2 | 11/2011 | Suh |
| 8,123,788 B2 | 2/2012 | Michelson |
| 8,128,628 B2 | 3/2012 | Freid et al. |
| 8,137,403 B2 | 3/2012 | Michelson |
| 8,167,946 B2 | 5/2012 | Michelson |
| 8,182,518 B2 | 5/2012 | Butler et al. |
| 8,206,399 B2 | 6/2012 | Gill et al. |
| 8,216,316 B2 | 7/2012 | Kirschman |
| 8,231,633 B2 | 7/2012 | Lim et al. |
| 8,275,594 B2 | 9/2012 | Lin et al. |
| 8,287,575 B2 | 10/2012 | Murner et al. |
| 8,287,576 B2 | 10/2012 | Barrus |
| 8,298,235 B2 | 10/2012 | Grinberg et al. |
| 8,298,272 B2 | 10/2012 | Edie et al. |
| 8,323,343 B2 | 12/2012 | Michelson |
| 8,328,872 B2 | 12/2012 | Duffield et al. |
| 8,343,220 B2 | 1/2013 | Michelson |
| 8,349,015 B2 | 1/2013 | Bae et al. |
| 8,353,958 B2 | 1/2013 | Edie et al. |
| 8,353,959 B2 | 1/2013 | Michelson |
| 8,398,688 B2 | 3/2013 | Peukert et al. |
| 8,403,986 B2 | 3/2013 | Michelson |
| 8,425,530 B2 | 4/2013 | Winslow et al. |
| 8,439,977 B2 | 5/2013 | Kostuik et al. |
| 8,449,585 B2 | 5/2013 | Wallenstein et al. |

(56) References Cited

U.S. PATENT DOCUMENTS

| | | |
|---|---|---|
| 8,491,598 B2 | 7/2013 | Crook |
| 8,491,654 B2 | 7/2013 | Frey et al. |
| 8,540,725 B2 | 9/2013 | Lim et al. |
| 8,562,655 B2 | 10/2013 | Butler |
| 8,584,853 B2 | 11/2013 | Knight et al. |
| 8,585,761 B2 | 11/2013 | Theofilos |
| 8,590,157 B2 | 11/2013 | Kruth et al. |
| 8,636,738 B2 | 1/2014 | McClintock et al. |
| 8,636,804 B2 | 1/2014 | Errico et al. |
| 8,641,768 B2 | 2/2014 | Duffield et al. |
| 8,668,741 B2 | 3/2014 | Michelson |
| 8,673,011 B2 | 3/2014 | Theofilos et al. |
| 8,696,681 B2 | 4/2014 | Harris et al. |
| 8,697,231 B2 | 4/2014 | Longepied et al. |
| 8,709,083 B2 | 4/2014 | Duffield et al. |
| 8,728,387 B2 | 5/2014 | Jones et al. |
| 8,734,491 B2 | 5/2014 | Seavey |
| 8,740,983 B1 | 6/2014 | Arnold et al. |
| 8,784,721 B2 | 7/2014 | Philippi et al. |
| 8,795,341 B2 | 8/2014 | Walker et al. |
| 8,801,791 B2 | 8/2014 | Soo et al. |
| 8,808,304 B2 | 8/2014 | Weiman et al. |
| 8,814,919 B2 | 8/2014 | Barrus et al. |
| 8,843,229 B2 | 9/2014 | Vanasse et al. |
| 8,864,829 B1 | 10/2014 | Bruffey et al. |
| 8,870,930 B2 | 10/2014 | Carbone et al. |
| 8,870,957 B2 | 10/2014 | Vraney et al. |
| 8,876,835 B2 | 11/2014 | Petit |
| 8,882,813 B2 | 11/2014 | Jones et al. |
| 8,882,814 B2 | 11/2014 | Suh |
| 8,882,840 B2 | 11/2014 | Mcclintock et al. |
| 8,882,843 B2 | 11/2014 | Michelson |
| 8,894,694 B2 | 11/2014 | Brandon |
| 8,903,533 B2 | 12/2014 | Eggers et al. |
| 8,906,097 B2 | 12/2014 | Mather et al. |
| 8,926,703 B2 | 1/2015 | Michelson |
| 8,932,356 B2 | 1/2015 | Kraus |
| 8,945,227 B2 | 2/2015 | Kirschman |
| 8,967,990 B2 | 3/2015 | Weidinger et al. |
| 8,999,711 B2 | 4/2015 | Harlow et al. |
| 9,011,982 B2 | 4/2015 | Muller et al. |
| 9,017,412 B2 | 4/2015 | Wolters et al. |
| 9,028,498 B2 | 5/2015 | Hershgold et al. |
| 9,101,321 B1* | 8/2015 | Kieser ............... A61B 6/4494 |
| 9,131,969 B2 | 9/2015 | Lorio et al. |
| 9,135,374 B2 | 9/2015 | Jones et al. |
| 9,173,750 B2 | 11/2015 | Weiman et al. |
| 9,180,010 B2 | 11/2015 | Dong et al. |
| 9,192,419 B2 | 11/2015 | McDonough et al. |
| 9,192,483 B1 | 11/2015 | Radcliffe et al. |
| 9,198,769 B2 | 12/2015 | Perrow et al. |
| 9,237,957 B2 | 1/2016 | Klimek et al. |
| 9,248,027 B2 | 2/2016 | Dunworth et al. |
| 9,248,028 B2 | 2/2016 | Gamache |
| 9,277,943 B2 | 3/2016 | Holly et al. |
| 9,283,078 B2 | 3/2016 | Roels et al. |
| 9,301,854 B2 | 4/2016 | Moskowitz et al. |
| 9,326,861 B2 | 5/2016 | Iott et al. |
| 9,327,359 B2 | 5/2016 | Wotruba |
| 9,351,849 B2 | 5/2016 | Mather et al. |
| 9,358,123 B2 | 6/2016 | McLuen et al. |
| 9,358,127 B2 | 6/2016 | Duffield et al. |
| 9,364,343 B2 | 6/2016 | Duffield et al. |
| 9,381,045 B2 | 7/2016 | Donner et al. |
| 9,381,093 B1 | 7/2016 | Morris et al. |
| 9,393,049 B2 | 7/2016 | Jones et al. |
| 9,402,735 B2 | 8/2016 | McDonough et al. |
| 9,427,330 B2 | 8/2016 | Petersheim et al. |
| 9,445,851 B2 | 9/2016 | Walker et al. |
| 9,456,901 B2 | 10/2016 | Jones et al. |
| 9,463,098 B2 | 10/2016 | Michelson |
| 9,480,577 B2 | 11/2016 | Despiau et al. |
| 9,510,957 B2 | 12/2016 | Weiman et al. |
| 9,566,163 B2 | 2/2017 | Suddaby et al. |
| 9,572,680 B2 | 2/2017 | Theofilos et al. |
| 9,585,762 B2 | 3/2017 | Suddaby et al. |
| 9,615,838 B2 | 4/2017 | Nino et al. |
| 9,615,936 B2 | 4/2017 | Duffield et al. |
| 9,675,467 B2 | 6/2017 | Duffield et al. |
| 9,693,876 B1 | 7/2017 | Mesiwala |
| 9,757,163 B2 | 9/2017 | Jacene et al. |
| 9,833,333 B2 | 12/2017 | Duffield et al. |
| 9,848,996 B2 | 12/2017 | Faulhaber |
| 9,855,150 B2 | 1/2018 | Altarac et al. |
| 9,895,237 B2 | 2/2018 | Seifert et al. |
| 9,913,732 B2 | 3/2018 | Kana et al. |
| 9,918,848 B2 | 3/2018 | Waugh et al. |
| 9,987,051 B2 | 6/2018 | Nunley et al. |
| D824,518 S | 7/2018 | Wilson et al. |
| 10,028,841 B2 | 7/2018 | Moore et al. |
| 10,098,760 B2 | 10/2018 | Urban et al. |
| 10,166,115 B2 | 1/2019 | Kana et al. |
| 10,188,524 B2 | 1/2019 | Buss |
| 10,238,502 B2 | 3/2019 | Prado et al. |
| 10,327,910 B2 | 6/2019 | Kirschman |
| 10,342,678 B2 | 7/2019 | Flores et al. |
| 10,543,101 B1* | 1/2020 | Suh ..................... A61F 2/4455 |
| 10,850,193 B2 | 12/2020 | DeRidder et al. |
| 11,000,321 B2 | 5/2021 | White et al. |
| 11,116,645 B2 | 9/2021 | Zakelj |
| 11,259,937 B2 | 3/2022 | Shi et al. |
| 11,298,747 B2 | 4/2022 | Klein et al. |
| 2001/0047207 A1 | 11/2001 | Michelson |
| 2001/0047208 A1 | 11/2001 | Michelson |
| 2002/0128714 A1 | 9/2002 | Manasas et al. |
| 2003/0040798 A1 | 2/2003 | Michelson |
| 2003/0135276 A1 | 7/2003 | Eckman |
| 2003/0149438 A1 | 8/2003 | Nichols et al. |
| 2004/0010259 A1 | 1/2004 | Keller et al. |
| 2004/0024400 A1 | 2/2004 | Michelson |
| 2004/0098129 A1 | 5/2004 | Lin |
| 2004/0153089 A1 | 8/2004 | Zdeblick et al. |
| 2004/0243237 A1 | 12/2004 | Unwin et al. |
| 2004/0249471 A1 | 12/2004 | Bindseil et al. |
| 2005/0021151 A1 | 1/2005 | Landis |
| 2005/0149192 A1 | 7/2005 | Zucherman et al. |
| 2005/0177238 A1 | 8/2005 | Khandkar et al. |
| 2005/0283245 A1 | 12/2005 | Gordon et al. |
| 2006/0058888 A1 | 3/2006 | Hunter et al. |
| 2007/0016218 A1 | 1/2007 | Winslow et al. |
| 2007/0116734 A1 | 5/2007 | Akash |
| 2007/0233272 A1 | 10/2007 | Boyce et al. |
| 2008/0281425 A1 | 11/2008 | Thalgott et al. |
| 2008/0287957 A1 | 11/2008 | Hester et al. |
| 2009/0093881 A1 | 4/2009 | Bandyopadhyay et al. |
| 2009/0105831 A1 | 4/2009 | Jones et al. |
| 2009/0210062 A1 | 8/2009 | Thalgott et al. |
| 2009/0270922 A1 | 10/2009 | Biedermann et al. |
| 2009/0291308 A1 | 11/2009 | Pfister et al. |
| 2010/0100131 A1 | 4/2010 | Wallenstein |
| 2010/0100138 A1 | 4/2010 | Reynolds et al. |
| 2010/0137990 A1 | 6/2010 | Apatsidis et al. |
| 2010/0228369 A1 | 9/2010 | Eggers et al. |
| 2010/0256760 A1 | 10/2010 | Hansell |
| 2010/0312282 A1 | 12/2010 | Abdou |
| 2011/0144752 A1 | 6/2011 | Defelice et al. |
| 2011/0165340 A1 | 7/2011 | Baumann |
| 2011/0168091 A1 | 7/2011 | Baumann et al. |
| 2011/0190904 A1 | 8/2011 | Lechmann et al. |
| 2011/0264152 A1 | 10/2011 | Weiman et al. |
| 2011/0301709 A1 | 12/2011 | Kraus et al. |
| 2012/0046750 A1 | 2/2012 | Obrigkeit et al. |
| 2012/0143334 A1 | 6/2012 | Boyce et al. |
| 2012/0158062 A1 | 6/2012 | Nunley et al. |
| 2012/0179261 A1 | 7/2012 | Soo |
| 2012/0191188 A1 | 7/2012 | Huang |
| 2012/0191189 A1 | 7/2012 | Huang |
| 2012/0277803 A1 | 11/2012 | Remesh et al. |
| 2012/0277870 A1 | 11/2012 | Wolters et al. |
| 2012/0277873 A1 | 11/2012 | Kana et al. |
| 2012/0310364 A1 | 12/2012 | Li et al. |
| 2013/0006314 A1 | 1/2013 | Mueller |
| 2013/0046345 A1 | 2/2013 | Jones et al. |
| 2013/0046348 A1 | 2/2013 | Black |

(56) References Cited

U.S. PATENT DOCUMENTS

| | | | |
|---|---|---|---|
| 2013/0110243 A1 | 5/2013 | Patterson et al. | |
| 2013/0116793 A1 | 5/2013 | Kloss | |
| 2013/0123925 A1* | 5/2013 | Patterson | A61B 17/8033 |
| | | | 623/17.16 |
| 2013/0171019 A1 | 7/2013 | Gessler et al. | |
| 2013/0197645 A1 | 8/2013 | Assell et al. | |
| 2013/0218276 A1 | 8/2013 | Fiechter et al. | |
| 2013/0245697 A1 | 9/2013 | Hulliger | |
| 2013/0273131 A1 | 10/2013 | Frangov et al. | |
| 2013/0345813 A1 | 12/2013 | Frank et al. | |
| 2014/0066997 A1 | 3/2014 | Humphreys | |
| 2014/0086780 A1 | 3/2014 | Miller et al. | |
| 2014/0088716 A1 | 3/2014 | Zubok et al. | |
| 2014/0107785 A1 | 4/2014 | Geisler et al. | |
| 2014/0107786 A1 | 4/2014 | Geisler et al. | |
| 2014/0172111 A1 | 6/2014 | Lang et al. | |
| 2014/0200670 A1 | 7/2014 | Chin et al. | |
| 2014/0277503 A1 | 9/2014 | Mendel et al. | |
| 2015/0018956 A1 | 1/2015 | Steinmann et al. | |
| 2015/0045924 A1 | 2/2015 | Cluckers et al. | |
| 2015/0134063 A1 | 5/2015 | Steinmann et al. | |
| 2015/0142158 A1 | 5/2015 | Szwedka | |
| 2015/0216573 A1 | 8/2015 | Chin et al. | |
| 2015/0272628 A1 | 10/2015 | Kishan et al. | |
| 2015/0328005 A1 | 11/2015 | Padovani et al. | |
| 2015/0328009 A1 | 11/2015 | Zappacosta et al. | |
| 2015/0352784 A1 | 12/2015 | Lechmann et al. | |
| 2015/0367575 A1 | 12/2015 | Roels et al. | |
| 2016/0058575 A1 | 3/2016 | Sutterlin, III et al. | |
| 2016/0106553 A1 | 4/2016 | Melkent et al. | |
| 2016/0128737 A1 | 5/2016 | Coric et al. | |
| 2016/0151171 A1 | 6/2016 | Mozeleski et al. | |
| 2016/0157908 A1 | 6/2016 | Cawley et al. | |
| 2016/0166396 A1 | 6/2016 | McClintock | |
| 2016/0213488 A1 | 7/2016 | Moore et al. | |
| 2016/0220388 A1 | 8/2016 | Flores et al. | |
| 2016/0235448 A1 | 8/2016 | Seex | |
| 2016/0235548 A1 | 8/2016 | McLaughlin et al. | |
| 2016/0270920 A1 | 9/2016 | Dawson et al. | |
| 2016/0361177 A1 | 12/2016 | Biedermann et al. | |
| 2017/0056199 A1 | 3/2017 | Altarac et al. | |
| 2017/0079807 A1 | 3/2017 | Wallenstein et al. | |
| 2017/0189204 A1 | 7/2017 | Riemhofer et al. | |
| 2017/0196606 A1 | 7/2017 | Cianfrani et al. | |
| 2017/0245998 A1 | 8/2017 | Padovani et al. | |
| 2017/0340358 A1 | 11/2017 | Bullard | |
| 2018/0318099 A1 | 11/2018 | Altarac et al. | |
| 2018/0318100 A1 | 11/2018 | Altarac et al. | |
| 2018/0338841 A1* | 11/2018 | Miller | A61B 17/80 |
| 2019/0008562 A1 | 1/2019 | Melton et al. | |
| 2019/0038319 A1 | 2/2019 | Tempco et al. | |
| 2019/0133778 A1 | 5/2019 | Johnston | |
| 2019/0314160 A1 | 10/2019 | Wang et al. | |
| 2019/0343650 A1* | 11/2019 | Petersheim | A61F 2/30771 |
| 2020/0046512 A1* | 2/2020 | Newman | A61F 2/4611 |
| 2020/0246162 A1 | 8/2020 | Schultz et al. | |
| 2021/0077268 A1 | 3/2021 | Struck et al. | |
| 2021/0153879 A1 | 5/2021 | Walsh et al. | |
| 2021/0154022 A1 | 5/2021 | Walsh et al. | |
| 2021/0379884 A1 | 12/2021 | O'Neill et al. | |

FOREIGN PATENT DOCUMENTS

| | | |
|---|---|---|
| EP | 0425542 B1 | 3/1995 |
| EP | 1464307 A1 | 10/2004 |
| EP | 1905391 B1 | 1/2010 |
| EP | 2145913 A1 | 1/2010 |
| EP | 2457538 A1 | 5/2012 |
| EP | 2865347 A1 | 4/2015 |
| EP | 1772108 B1 | 11/2015 |
| EP | 3415108 A1 | 12/2018 |
| EP | 3474783 A2 | 5/2019 |
| JP | 2008513120 A | 5/2008 |
| JP | 2009516544 A | 4/2009 |
| JP | 2009261947 A | 11/2009 |
| JP | 2013516235 A | 5/2013 |
| JP | 2015208669 A | 11/2015 |
| JP | 2015532858 A | 11/2015 |
| JP | 2015213530 A | 12/2015 |
| WO | 9000037 A1 | 1/1990 |
| WO | 9405235 A1 | 3/1994 |
| WO | 9419174 A1 | 9/1994 |
| WO | 9510248 A1 | 4/1995 |
| WO | 9532673 A1 | 12/1995 |
| WO | 9608360 A1 | 3/1996 |
| WO | 9628117 A1 | 9/1996 |
| WO | 9640015 A1 | 12/1996 |
| WO | 9640019 A1 | 12/1996 |
| WO | 9734546 A1 | 9/1997 |
| WO | 0025707 A1 | 5/2000 |
| WO | 0040177 A1 | 7/2000 |
| WO | 0066045 A1 | 11/2000 |
| WO | 0202151 A2 | 1/2002 |
| WO | 0230337 A2 | 4/2002 |
| WO | 02080820 A1 | 10/2002 |
| WO | 2006101837 A2 | 9/2006 |
| WO | 2009068021 A1 | 6/2009 |
| WO | 2010011849 A1 | 1/2010 |
| WO | 2011006155 A1 | 1/2011 |
| WO | 2011030017 A1 | 3/2011 |
| WO | 2011156504 A2 | 12/2011 |
| WO | 2012141715 A1 | 10/2012 |
| WO | 201317647 A1 | 2/2013 |
| WO | 2013155500 A1 | 10/2013 |
| WO | 2013156545 A1 | 10/2013 |
| WO | 201496294 A1 | 6/2014 |
| WO | 2014145527 A2 | 9/2014 |
| WO | 2016112175 A1 | 7/2016 |
| WO | 2017027873 A1 | 2/2017 |
| WO | 2018002711 A2 | 1/2018 |

OTHER PUBLICATIONS

Extended European Search Report for EP 16 15 2952 dated Jul. 1, 2016.
Fukuda A, Takemoto M, Tanaka K, Fujibayashi S, Pattanayak DK, Matsushita T, Sasaki K, Nishida N, Kokubo T, Nakamura T. Bone ingrowth into pores of lotus stem-type bioactive titanium implants fabricated using rapid prototyping technique. Bioceramics Development and Applications. Jan. 1, 2011;1, 3 pages.
Williams et al., CT Evaluation of Lumbar Interbody Fusion: Current Concepts, AJNR Am J Neuroradiol 26:2057-2066, Sep. 2005.
Cunningham et al, Design of Interbody Fusion Cages: Historical Considerations and Current Perspectives in Cage Technology; Surgical Techniques, Spinal Implants, pp. 421-465, 2006.
Akamaru et al., Healing of Autologous Bone in a Titanium Mesh Cage Used in Anterior Column Reconstruction After Total Spondylectomy; Spine vol. 27, No. 13, pp. E329-E333, 2002.
Lin et al., Interbody Fusion Cage Design Using Integrated Global Layout and Local Microstructure Topology Optimization; Spine, vol. 29, No. 16, pp. 1747-1754, 2004.
McAfee, Interbody Fusion Cages in Reconstructive Operations on the Spine, The Journal of Bone and Joint Surgery Incorporated, vol. 81A, No. 6, Jun. 1999, pp. 859-880.
Zdeblick, et al., LT-CAGE Lumbar Tapered Fusion Device Surgical Technique, Medtronic, pp. 1-25, 2000.
Kuslich, Lumbar Interbody Cage Fusion for Back Pain: An Update on the Bak (Bagby and Kuslich) System, Spine: State of the Art Reviews; vol. 13, No. 2, May 1999, pp. 295-311.
Cheung et al., Spinal Instrumentation Overview in Lumbar Degenerative Disorders: Cages, Lumbar Spine: Official Publication of the International Society for the Study of Lumbar Spine (3), pp. 286-291, 2004.
Sasso, Screws, Cages or Both?, <http://www.spineuniverse.com/professional/technology/surgical/thoracic/>, pp. 1-11, Sep. 2012.
Costa et al., Stand-alone cage for posterior lumbar interbody fusion in the treatment of high-degree degenerative disc disease: design of a new device for an "old" technique. A prospective study on a series of 116 patients, Eur Spine J, May 2011: 20 (Suppl 1), pp. 46-56.

(56) References Cited

OTHER PUBLICATIONS

Lin, et al. Structural and mechanical evaluations of a topology optimized titanium interbody fusion cage fabricated by selective laser melting process, Journal of Biomedical Materials Research Part A DOI 10.1 002/jbm.a, pp. 272-279, Apr. 2007.
Chong et al., The design evolution of interbody cages in anterior cervical discectomy and fusion: a systematic review; BMC Musculoskeletal Disorders Apr. 2015 16:99, pp. 1-20.
Bridwell et al.., Specialty Update, What's New in Spine Surgery, The Journal of Bone and Joint Surgery, Incorporated, pp. 1022-1030, Core 1st page of article, Jun. 2015.
EBI Spine, Promotional flyer, 1 page 2005.
Synthes Contact Fusion Cage, Technique Guide, 2007, pp. 1-16.
Stryker, TIritanium basic science summary, technical monograph, pp. 1-2, 2016.
Sofamar Danek Interfix Thread Fusion Device, pp. 32-45, 1999.
Kim et al. Spinal Instrumentation Surgical Techniques, Thieme Medical publishers, 2004, pp. 232-245, 518-524, p. 32-537, 736-743, 795-800.
Schultz, Christian K., et al., U.S. Appl. No. 62/478,162, filed Mar. 29, 2017, titled "Spinal Implant System".
Willis, Steven, et al., U.S. Appl. No. 14/994,749, filed Jan. 13, 2016, titled "Spinal Implant With Porous and Solid Surfaces".
ACP 1 Anterior Cervical Plating System, Surgical Technique, Stryker Spine, 2016.
Extended European Search Report and Written Opinion for EP Application No. 18173999.6, mailed Nov. 19, 2018.
Extended European Search Report for Application No. EP18827686. 9, dated Jun. 29, 2020, pp. 1-3.
Nuvasive., Base Interfixated Titanium: Rebuilding Spinal Foundation, 2016, 6 pages.
Globus Medical; Independence MIS: Anterior Lumbar Interbody Fushion System; 2017; 56 pages.
Medacta International; MectaLIF Anterior: Anterior Lumbar Interbody Fushion Device: Apr. 2017; 2 pages.
Nuvasive: Speed of Innovation: Brigade: Standalone ALIF: Surgical Technique; 2015, 28 pages.
Nuvasive; Speed of Innovation—Coroent Small Interlock Stand-alone Cervical Interbody Fixation Designed for Simplicity and Versatility, © 2011, 8 pages.
SeaSpine: The Next Wave in Spine Technology—Zuma-C Cervical Stabilization System, © 2011, 13 pages.
DePuy Synthes, companies of Johnson & Johnson—Zero-P VA Surgical Technique, 2016, 52 pages.
DePuy Synthes, Part of the Johnson & Johnson Family of Companies—Zero-P and Zero-P chronOS: Zero profile anterior cervical interbody fusion (ACIF) device, 2016, 72 pages.
Medtronic—Divergencetm Stand-Alone Interbody Cage Preoperative planning guide and surgical technique, © 2015, 24 pages.
Zimmer Biomet—Optio-C® Anterior Cervical PEEK Interbody System Surgical Technique Guide, © 2017, 36 pages.
Globus Medical—Coalition Stand-Alone ACDF System, © 2013, 6 pages.
Unison—C Anterior Cervical Fixation System; 2018, 3 pages.
Zavation Z-Link Cervical; 2018; 13 pages.
Precision Spine: Vault C: ACDF System; 2015, 8 pages.
Styrker Spine: AVS Anchor-C Cervical Cage System; 2014; 2 pages.
Spine Smith: IN:C2—Now Open for Fusion; 2012, 2 pages.
Amendia: Spinal Elements; CERES-C: Stand-Alone Interbody: MM-156, May 17, 2018; Rev. 1; 2 pages.
Stryker: Aero-C: Anterior Cervical Interboby and Fixation System; Apr. 2016; 28 pages.
Stryker Spine: AVS Anchor-L: Lumbar Cage System; Jul. 2013, 2 pages.
European Search Report for EP20154502.7 issued Jul. 10, 2020; 3 pages.
European Extended Search Report for EP20196447.5 dated Feb. 15, 2021, 3 pages.

\* cited by examiner

SECTION AA-AA

SECTION P-P

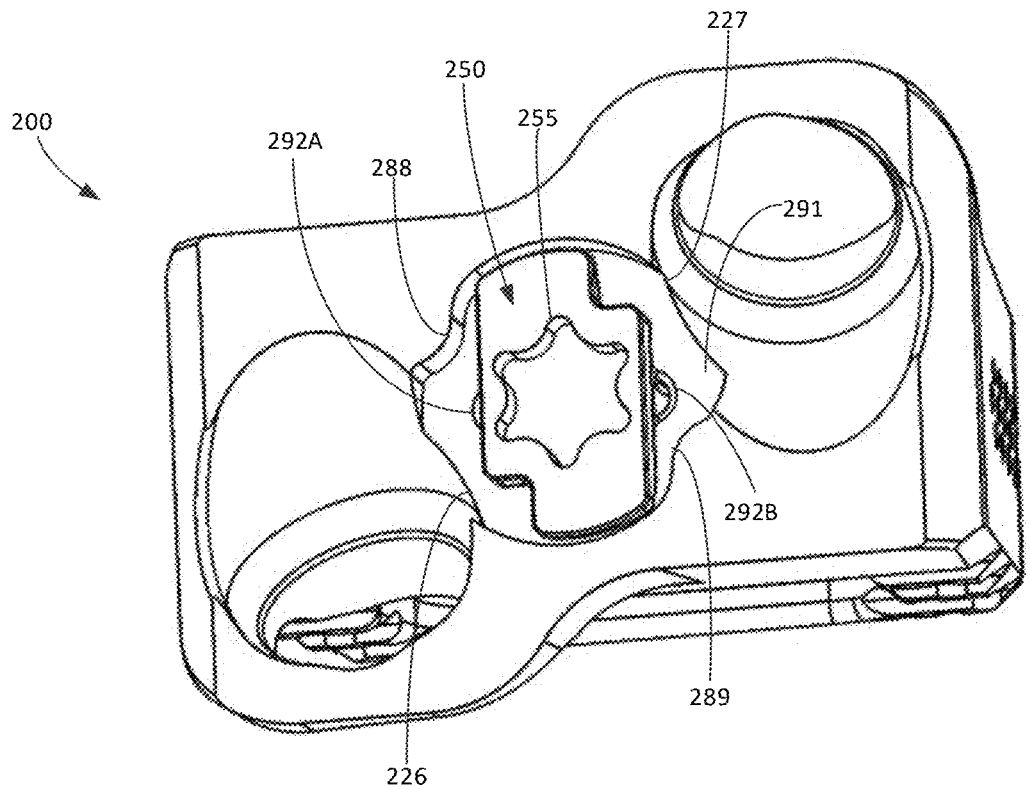
FIG. 2D
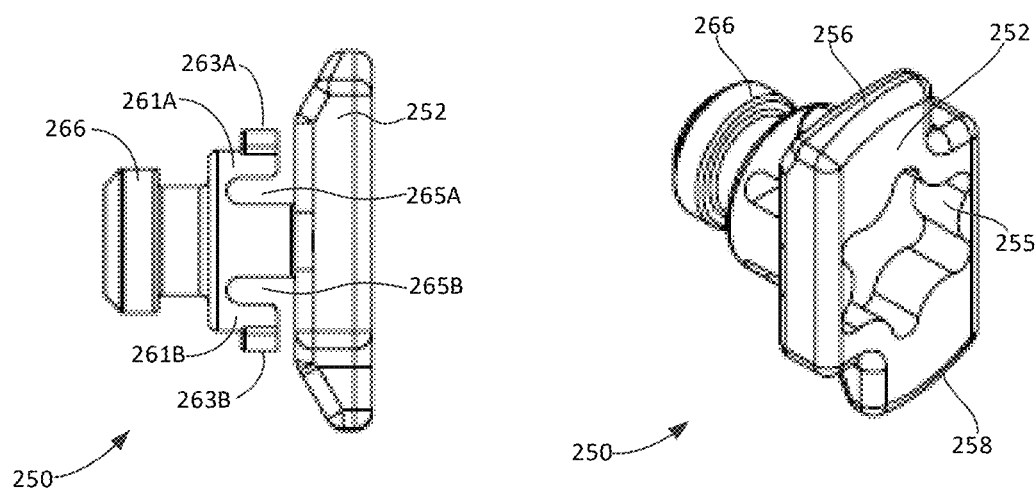
FIG. 2E
FIG. 2F

SECTION T-T

SECTION L-L

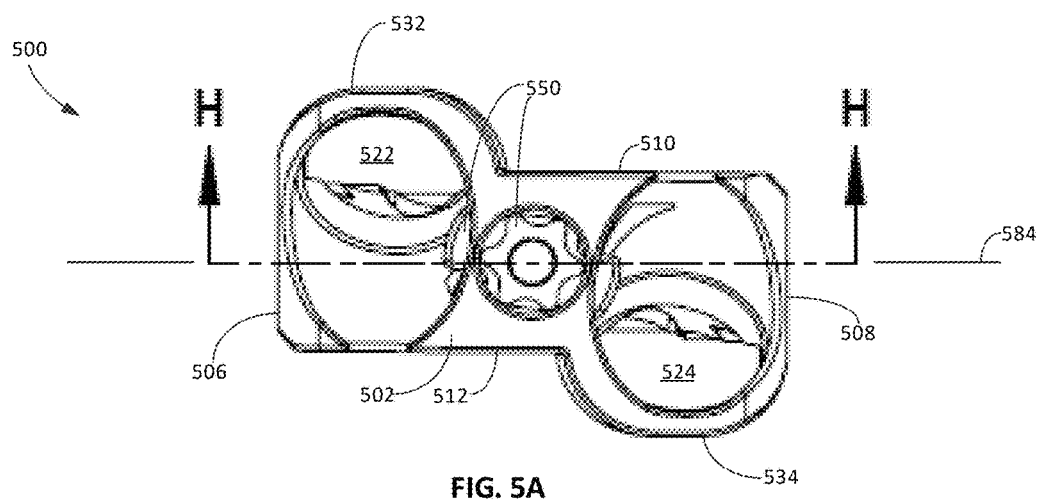
FIG. 5A
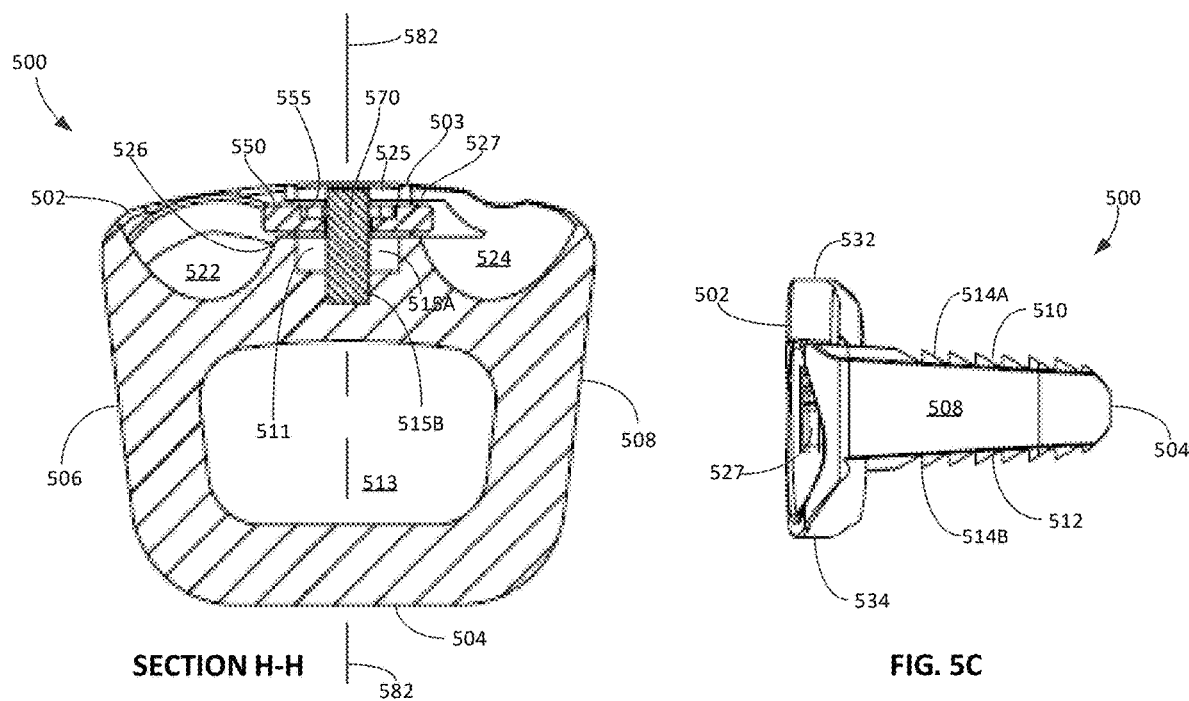
SECTION H-H
FIG. 5B
FIG. 5C

SECTION E-E

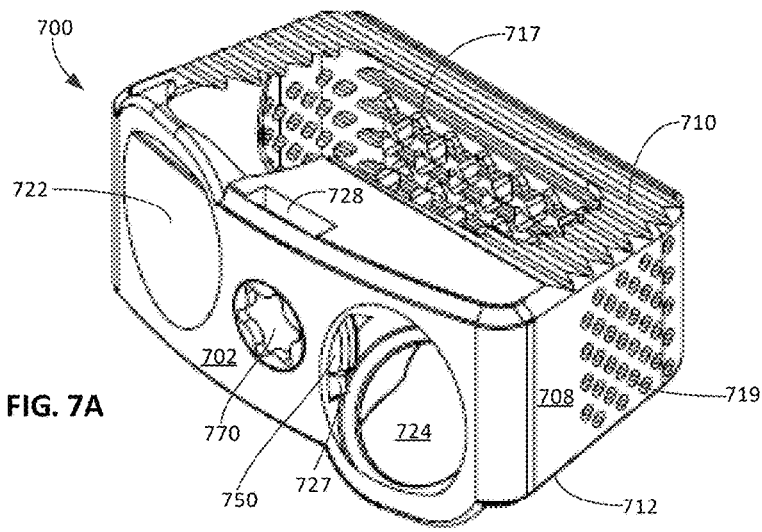
FIG. 7A
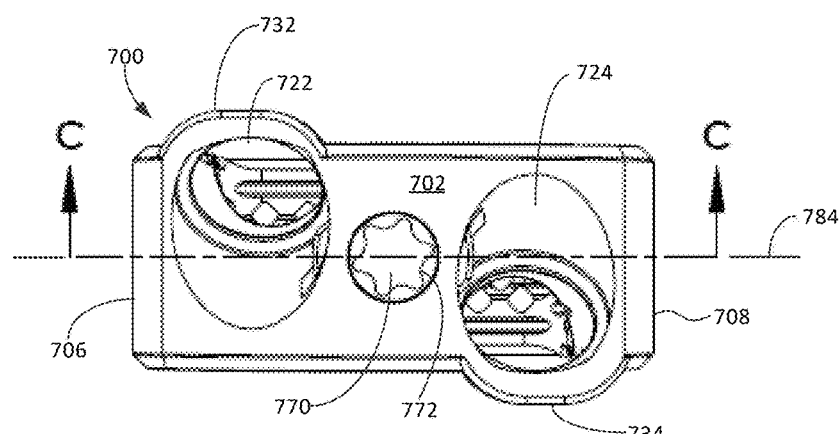
FIG. 7B
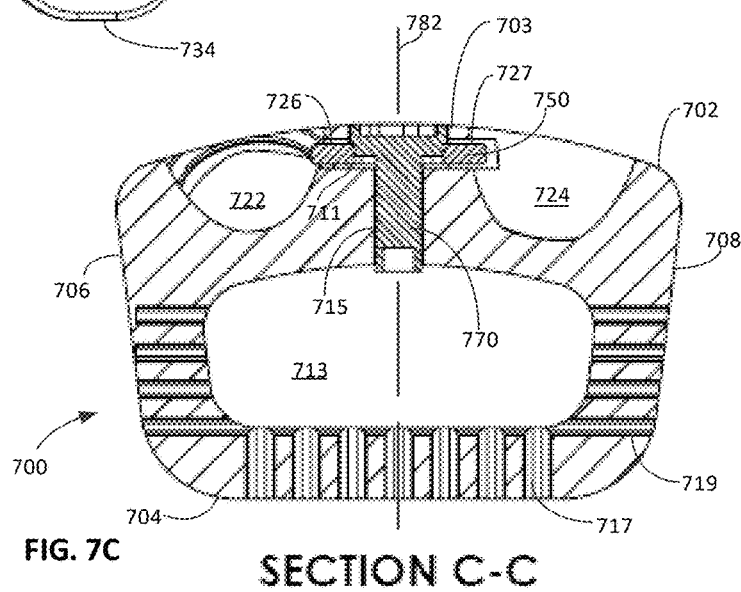
FIG. 7C    SECTION C-C

SECTION M-M

3D PRINTED CERVICAL STANDALONE IMPLANT

CROSS REFERENCE TO RELATED APPLICATION

This application is a continuation of U.S. patent application Ser. No. 17/019,912, filed Sep. 14, 2020, which claims the benefit of the filing date of U.S. Provisional Patent Application No. 62/900,937, filed Sep. 16, 2019, the disclosures of which are hereby incorporated by reference herein in their entirety.

BACKGROUND OF THE INVENTION

New implant technologies and associated methodologies are sought on an ongoing basis to improve outcomes of spinal surgery. When an implant is designed for use in an intervertebral space, the implant may serve to treat degenerative disc disease, misalignment of vertebral bodies, radiculopathy or myelopathy due to compression of the spine, or trauma (including that associated with a tumor), among other conditions.

Past improvements to spinal implant technology have included improvements for interbodies with supplemental fixation, such as plates and screws or pedicle screws and associated components and in other cases, improvements for standalone intervertebral cages. Standalone cage designs typically include two, three or four screws for fixation of the cage to adjacent vertebrae. In more recent developments, some designs have incorporated a locking element to prevent back out of screws once the screws are disposed in the cage and anchored to bone.

However, existing designs often have screw openings that provide a trajectory for the screws that undesirably directs the screws into a vertebra at a shallow angle. Further, to the extent existing designs may have protruding surfaces surrounding the screw openings in the cage to aid in obtaining a desired screw trajectory, such designs often require the assembly of two separate components to form a complete cage. Additionally, existing designs with locking mechanisms may suffer from the locking mechanism becoming disengaged from a surface of the cage over time due to its open exposure on one side of the cage.

Thus, a need exists for improved intervertebral implants and improved methods of manufacturing and implantation of intervertebral implants.

BRIEF SUMMARY OF THE INVENTION

In one aspect, the present disclosure relates to an intervertebral implant. In one embodiment, the intervertebral implant includes an implant body and a locking element. The implant body includes a leading surface and a trailing surface opposite the leading surface. The implant body also includes first and second passageways through the implant body, each passageway sized for the disposal of a bone fastener therein. Further, the implant body also includes a cavity in between the first and second passageways, the cavity defined by a plurality of internal walls that include a trailing wall that separates the cavity from the trailing surface. The locking element includes a screw drive element and is disposed in the cavity such that the drive element is visible through an access opening in the trailing wall. The locking element is rotatable about its center through actuation of the screw drive element such that in a first rotational position, a first part of the locking element is located within one of the first and second passageways and in a second rotational position, the first part of the locking element is inside the implant body covered by the trailing wall.

In some examples, the implant body may be monolithic. In some examples, the cavity may have a first perimeter measured in a plane parallel to the trailing surface and the access opening may have a second perimeter measured on the trailing surface. The first perimeter may entirely envelope the second perimeter when viewed facing the trailing surface. In some examples, the locking element may include a head that includes the first part of the locking element and a shaft that extends from the head. The shaft may engage with the body of the implant in the first rotational position and in the second rotational position. In some examples, the intervertebral implant may include a head that encompasses the first part of the first locking element. The head may have a width extending from a first end to a second end, the first end and the second end being inside the implant body and covered by the trailing wall in at least one rotational position of the locking element. In some examples, the shaft may include two separate parts extending longitudinally from the head of the locking element. In some examples, the locking element may include an internal cavity throughout its length along the central longitudinal axis.

In some examples, the locking element may include a pin disposed in an opening through the locking element, the pin engaging directly with implant body so that the locking element is prevented from sliding out of the cavity. In some example, the first part of the locking element may be slidable into the implant through a second access opening in one of the passageways and in communication with the cavity. The first part of the locking element may be oriented so that the screw drive element is facing the trailing wall as the first part is inserted into the second access opening. In some embodiments, the first part of the locking element may be slidable into the implant through a second access opening on an inferior surface or a superior surface of the implant body. The second access opening may be in communication with the cavity. In some examples, the first passageway may be defined in part by a protrusion on an inferior surface of the implant body. In some examples, the second passageway may be defined in part by a protrusion on a superior surface of the implant body opposite the inferior surface.

In some embodiments, the above described intervertebral implant may be formed through an additive manufacturing process. In particular, a method of forming the intervertebral implant may involve: forming the implant body of the intervertebral implant utilizing an additive layer manufacturing process; and inserting the locking element through a slot in the implant body, the slot being in communication with the cavity so that following insertion, the locking element is disposed in the cavity. In some examples, the method may include inserting a pin through the locking element and into the cavity, the pin engaging with the implant body so that the locking element is secured to the implant body. In some examples, the additive layer manufacturing process may be performed based on the execution of software that retrieves geometric and material parameters of the implant body stored in a database. In some embodiments, forming the implant may involve a continuous, single step additive manufacturing process.

In some embodiments, the above described intervertebral implant may be formed through an additive manufacturing process. In particular, a method of forming the intervertebral implant may involve: forming the implant body and the locking element of the intervertebral implant utilizing an additive layer manufacturing process. In some examples, forming the implant and the locking element may involve a continuous, single step additive manufacturing process. In some examples, the additive layer manufacturing process may be performed based on the execution of software that retrieves geometric and material parameters of the implant body and the locking element that are stored in a database.

In another embodiment, the intervertebral implant includes a monolithic implant body and a locking element. The monolithic implant body includes a leading surface and a trailing surface opposite the leading surface along with a superior surface and an inferior surface opposite the superior surface. The implant includes a protruding part on the inferior surface or the superior surface. The protruding part defines a portion of a fastener opening that is sized for receipt of a bone fastener. The fastener opening extends from the trailing surface to the inferior surface or the superior surface. The implant also includes a central opening extending into the implant body from the trailing surface. Turning to the locking element, the locking element is disposable in the central opening of the monolithic implant body. The locking element includes a first engagement feature for engagement with a complementary second engagement feature of the implant body within the central opening. When the locking element is engaged to the monolithic implant body, the locking element is rotatable into a first rotational position where a portion of the fastener opening is covered by a portion of the locking element and a second rotational position where the opening is unobstructed by the locking element.

In some examples, the implant may include a second protruding part, the second protruding part being on the inferior surface and defining a portion of a second fastener opening. The first protruding part may be on the superior surface. In some embodiments, the protruding part may form an arch shape over its length. In some embodiments, the fastener opening may be aligned along a first axis at an angle between 25 and 45 degrees relative to a central plane parallel to and in between the superior surface and the inferior surface. In some examples, the first axis may be at an angle of approximately 35 degrees relative to the central plane. In some examples, the second axis may be at an angle of approximately 35 degrees relative to the central plane.

In some examples, the locking element may be centered on a central plane parallel to and in between the superior surface and the inferior surface and a center of the fastener opening at the trailing surface may be offset relative to the central plane. In some examples, the first fastener opening has a first center at the trailing surface and the second fastener opening has a second center at the trailing surface. The first center may be on a first side of a central plane parallel to and in between the superior surface and the inferior surface and the second center may be on a second side of the central plane. In some examples, the locking element may include a central cavity therein. The central cavity may extend longitudinally through a head and a shaft extending from the head and be sized for the receipt of an insertion instrument engagement feature. In some examples, the body may include a first plurality of channels extending inward from the leading surface and a second plurality of channels extending from the superior surface to the inferior surface. In some examples, the first plurality of channels may have a first pattern and the second plurality of channels may have a second pattern, the second pattern being different from the first pattern.

In some embodiments, the intervertebral implant is part of a system that includes an insertion instrument. The insertion instrument may include a pair of prongs adapted to fit within the central cavity of the locking element. The insertion instrument may also include a shaft advanceable into a space in between the pair of prongs to cause the pair of prongs to spread apart from one another and apply force against the locking element, thereby engaging the insertion instrument with the implant body.

In another embodiment, the intervertebral implant includes an implant body and a locking element with flexible characteristics. The implant body includes a leading surface and a trailing surface opposite the leading surface. Within the implant body are first and second passageways, each passageway sized for the disposal of a bone fastener therein. The implant body also includes a recessed surface that is recessed relative to the trailing surface and has a length that extends from an edge of the first passageway to an edge of the second passageway. The recessed surface includes first and second dovetail grooves on sides of the recessed surface. Each dovetail groove extends from the edge of the first passageway to the edge of the second passageway. The locking element has a continuous perimeter with an opening therein, a width of the locking element being wider than a width of the recessed surface. Additionally, a length of the locking element is longer than the length of the recessed surface. The locking element is flexible such that it is insertable into the respective dovetail grooves of the implant body.

In another aspect, the present disclosure relates to a spinal implant system. The system includes an intervertebral implant and an insertion instrument. The intervertebral implant of the system includes a body with a leading surface and a trailing surface opposite the leading surface. The implant also includes a first opening within the body sized for the disposal of a bone fastener therein, the first opening extending from the trailing surface to an inferior surface of the body or a superior surface of the body. Similarly, the implant includes a second opening within the body, the second opening extending into the body from the trailing surface. Additionally, the implant also includes a hollow locking element that is engaged to the body within the second opening. The hollow locking element is rotatable about its axis to block and unblock the first opening. Turning to the insertion instrument, the insertion instrument includes an outer shaft with a cannulated body and two longitudinally extending prongs extending from an end of the cannulated body, each prong having a reverse taper toward a respective free end. The hollow locking element also includes an inner shaft axially translatable within the cannulated shaft. Additionally, the insertion instrument includes an actuation mechanism adapted to control axial translation of the inner shaft. When the two longitudinally extending prongs are within a hollow part of the hollow locking element and the inner shaft is translated distally from a first position remote from the two longitudinally extending prongs to a second position in between the two longitudinally extending prongs, the two longitudinally extending prongs become further apart to engage the locking element.

In some examples, the insertion instrument may also include first and second longitudinally extending arms positioned on opposite sides of the two longitudinally extending prongs, each longitudinally extending arm including an inward facing protrusion sized for engagement with a notch in the body of the intervertebral implant. In some examples, each of the first longitudinally extending arm and the second longitudinally extending arm may be biased so that respective distal ends of the arms are at a first distance from a central axis along the inner shaft and respective proximal ends of the arms are at a second distance from the central axis, the second distance greater than the first distance. In some examples, the body may include a first notch on a first side edge of the trailing surface and a second notch on a second side edge of the trailing surface, the notches adapted to receive the respective inward facing protrusions of the first and second longitudinally extending arms.

In some examples, the insertion instrument may include a distal region adjacent to the end of the cannulated body, the distal region being wider than the cannulated body and including an inserter opening therethrough. The inserter opening may have a first central longitudinal axis at a first angle relative to the inferior surface of the body such that when the insertion instrument is engaged with the body, the first central longitudinal axis through the inserter opening is coincident with a second central longitudinal axis through the first opening. In some examples, the locking element may be disposed at a center of the trailing surface. In some examples, the body may include a third opening within the body, the third opening sized for the disposal of a bone fastener therein and extending from the trailing surface to a superior surface of the body. The third opening may be positioned so that the second opening is in between the first opening and the third opening. In some examples, the system may include a drill guide slidably engageable with the insertion instrument. In some examples, the drill guide may include a first bore aligned at a first angle, and the first opening in the body may be aligned at the first angle. In some examples, the hollow part of the hollow locking element may be entirely within an actuatable drive element of the hollow locking element.

In another aspect, the present disclosure relates to a method of manufacturing an intervertebral implant. In one embodiment, the method may involve steps including: forming a first portion of the intervertebral implant using additive layer manufacturing, the first portion including at least part of an internal cavity sized for disposal of a locking element therein; after forming the first portion, inserting the locking element into the internal cavity; and, after inserting the locking element, forming a second portion of the intervertebral implant using additive layer manufacturing, the second portion including a wall at least partially enclosing the locking element within the intervertebral implant.

In some examples, the intervertebral implant may be formed through a subtractive form of manufacture. In some examples, the first portion and the second portion together may complete the formation of the intervertebral implant. In some examples, the method may include inserting a pin through the locking element and into the internal cavity of the intervertebral implant such that the locking element is prevented from disengaging from the intervertebral implant. In some examples, forming the first portion and the second portion may be based on details of the intervertebral implant design processed by an additive layer manufacturing machine.

In another embodiment, a method of manufacturing an intervertebral implant may involve forming an intervertebral implant and a locking element together using additive layer manufacturing in a single continuous step. Subsequent to formation through the single continuous step, the locking element is disposed within the intervertebral implant within a cavity that is internal to an outer perimeter of the intervertebral implant.

In yet another aspect, the present disclosure relates to a method of implanting an intervertebral implant into an intervertebral space. The method includes: inserting a locking element into a cavity of the intervertebral implant through a slot in an exterior surface of the intervertebral implant, a width of the cavity being greater than a width of the slot, the locking element being covered by an outer wall of the intervertebral implant once inserted; engaging an insertion instrument with the intervertebral implant; advancing the insertion instrument with the intervertebral implant into a prepared intervertebral space; positioning the implant within the prepared intervertebral space; inserting a bone fastener through a guide opening in the insertion instrument and subsequently through an opening in the intervertebral implant to anchor the bone fastener at an angle toward a corner of a vertebra adjacent to the prepared intervertebral space; removing the insertion instrument; and rotating the locking element to block the opening of the intervertebral implant to prevent back out of the bone fastener.

BRIEF DESCRIPTION OF THE DRAWINGS

The present disclosure will be better understood on reading the following detailed description of non-limiting embodiments thereof, and on examining the accompanying drawings, in which:

FIG. 2D is a sectional view of the implant and locking element of FIG. 2B.

FIGS. 2E-2F are views of the locking element of FIG. 2B.

FIGS. 5A-5C are various views of an implant with a locking element disposed therein according to another embodiment of the disclosure.

FIGS. 7A-7C are various views of an implant with a locking element disposed therein according to another embodiment of the disclosure.

DETAILED DESCRIPTION

As used herein in reference to an implant, e.g., interbody cage, the term "superior" refers to a portion of the implant nearer the patient's head, while the term "inferior" refers to a portion of the implant nearer the user's feet, when the implant is implanted in an intended position and orientation. As with the terms "superior" and "inferior," the term "anterior" refers to a portion of the implant nearer the front of the patient, the term "posterior" refers to a portion of the implant nearer the rear of the patient, the term "medial" refers to a portion of the implant nearer the mid-line of the patient, and the term "lateral" refers to a portion of the implant farther away from the mid-line of the patient. Additionally, the term "leading" refers to a portion of the implant that is inserted into the patient ahead of the remainder of the implant while conversely, the term "trailing" refers to a portion of the implant closest to an inserter instrument and is the last part of the implant inserted into the patient.

Figure 2A:
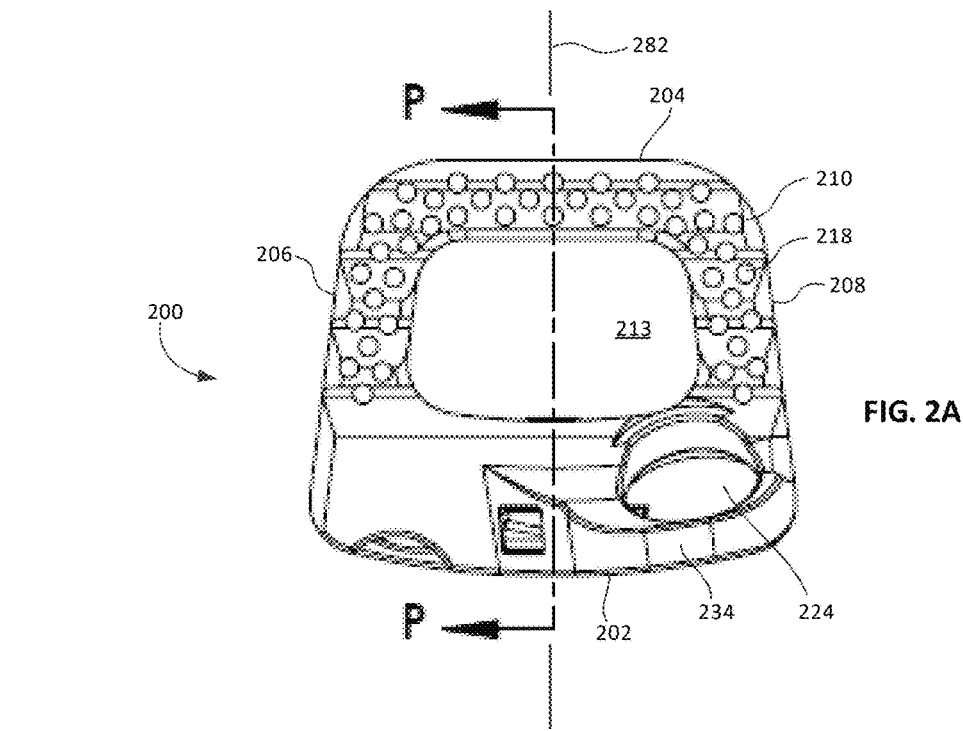
FIGS. 2A-2C are various views of an implant with a locking element disposed therein according to another embodiment of the disclosure.

In one aspect, the present disclosure relates to an implant including a locking element adapted for use in an intervertebral region within a spine. As shown and discussed, the implant is a standalone implant. Additionally, the implant is a monolithic structure and as such does not require assembly of separate parts to form an entirety of the structure. By way of example, the implant body may be monolithic with a separate locking element irremovably disposed therein. To form an implant in such a manner, including implants such as that shown in FIG. 2, employment of an additive manufacturing process is used because the combined implant and locking element cannot be manufactured using a subtractive manufacturing process. In some examples, additive manufacture may be layer-by-layer using an additive layer manufacturing ("ALM"), i.e., 3D printing, process. With formation of the implant using ALM, the need for assembly of multiple components is, in many instances, eliminated. Additionally, there is no need to build specialized inter-component engagement features into each of the separate components, as the implant is formed monolithically. In some examples, ALM processes are powder-bed based and involve one or more of selective laser sintering (SLS), selective laser melting (SLM), and electron beam melting (EBM), as disclosed in U.S. Pat. Nos. 7,537,664; 8,728,387; 9,180,010; and 9,456,901, the disclosures of which are hereby incorporated by reference in their entireties herein. Details of various step-by-step approaches to the ALM procedure that may be utilized to form the implant embodiments contemplated herein are discussed elsewhere in the present disclosure.

Figure 1A:
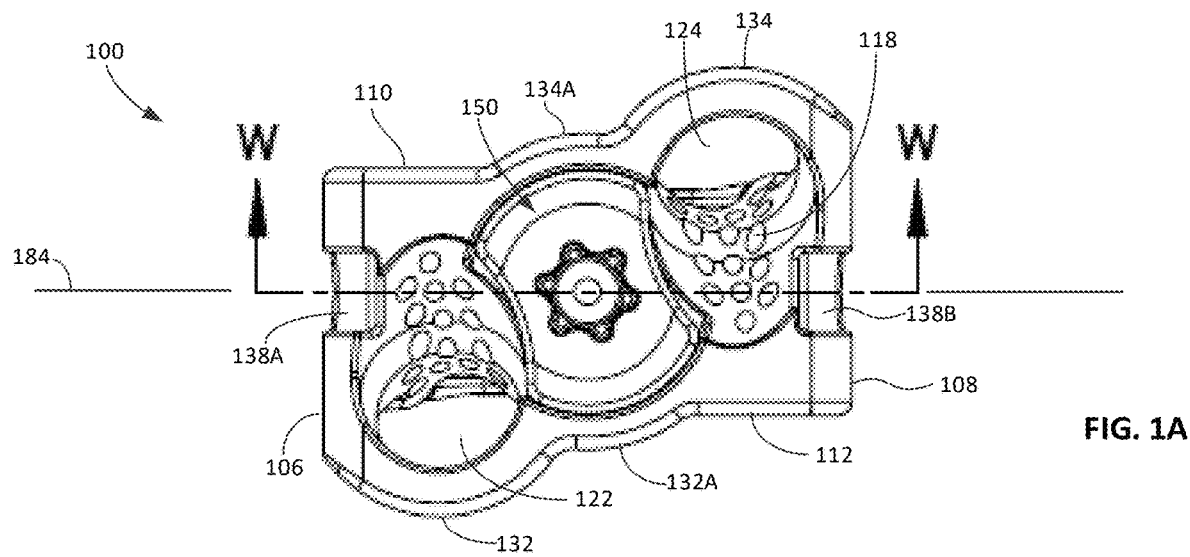
FIGS. 1A-1C are various views of an implant with a locking element disposed therein according to one embodiment of the disclosure.
Figure 1B:
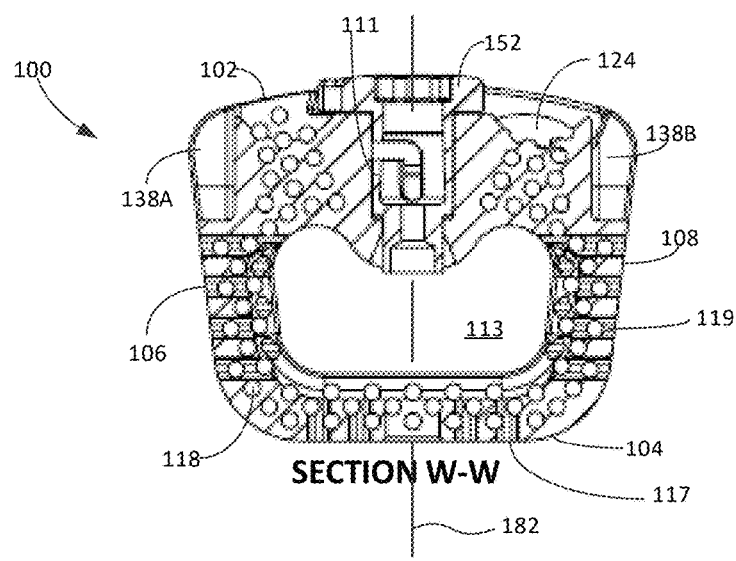
Figure 1C:
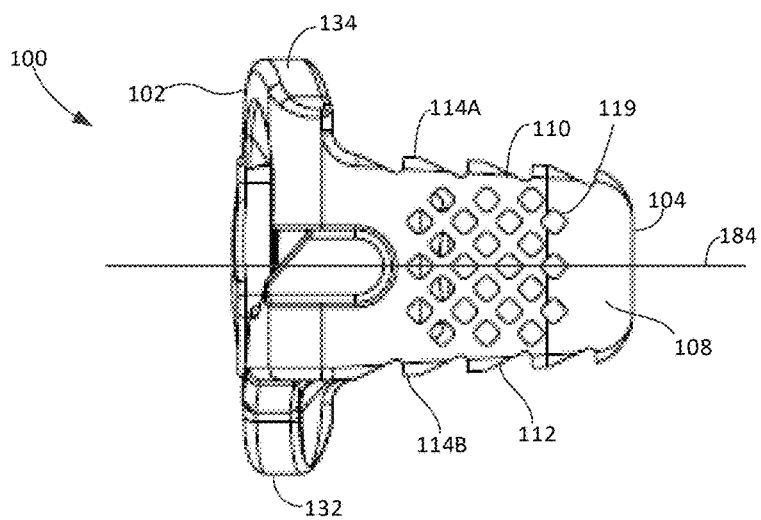

In one embodiment, implant 100 is an intervertebral cage as shown in FIGS. 1A-1C and includes a complementary locking element 150. As shown in FIG. 1C, the implant is generally shaped in the form a rectangular prism, though does include prominent protruding features adjacent to trailing surface 102.

Turning to the details of the external surfaces of implant 100, the implant includes a superior surface 110, an inferior surface 112, side surfaces 106, 108, a trailing surface 102 and a leading surface 104. Superior and inferior surfaces 110, 112 are generally parallel to one another though taper slightly from the trailing surface toward the leading surface while trailing surface 102 and leading surface 104 are generally parallel to one another, as shown in FIG. 1C. Side surfaces 106, 108 taper toward one another from the leading surface toward the trailing surface, as shown in FIG. 1B. The above described regions of the implant define a generally uniform profile, although adjacent to trailing surface 102, the above described external surfaces include protrusions, as shown in FIGS. 1A and 1C. In particular, superior surface 110 includes a protrusion in the form of ridge 134 while inferior surface 112 includes a protrusion in the form of ridge 132. These are described in greater detail below. It should be appreciated that in some alternative arrangements, the relationship between the various surfaces may vary from that shown. Additionally, each of superior surface 110 and inferior surface 112 includes a plurality of fins 114A, 114B, respectively, shown in FIG. 1C. Each fin is oriented so that a length of the fin extends from one side surface to the other.

Turning to the density of the implant structure, implant 100 includes lamellar features in the form of channels through a body of the implant, as best shown in FIGS. 1A-1C. The channels as shown are diamond shaped and provide the implant with a customized density and/or variation in density over the implant volume that may mirror that found in certain bone structures, e.g., lamellar patterns. In alternative arrangements, the channels may be circular, another shape, or have more than one shape among the channels of the implant. Further examples and embodiments of implants with various channel configurations are described in U.S. Pat. Nos. 9,987,051, 10,028,841 and D824,518, the disclosures of which are hereby incorporated by reference herein in their entirety.

In FIGS. 1A-1C, implant 100 includes three sets of channels, each oriented orthogonally relative to the other two. A first grouping of channels are side channels 119 that extend approximately parallel with trailing and leading surfaces 102, 104. As shown in FIG. 1C, side channels 119 are closely spaced and may be equidistant from one another measured in section approximately parallel to the side surfaces. Each channel is linear and includes a gap through central opening 113, as shown in FIG. 1B. In some examples, one or more channels may extend fully between the side surfaces of the implant. A second group of channels are vertical channels 118, best shown in FIGS. 1A and 1B. Each vertical channel 118 is oriented in the superior-inferior axis when the implant is disposed in a spine. Channels may be approximately equally spaced from one another and are distributed around a body of the implant on all sides of opening 113, as shown in FIG. 1B. Some of the individual channels of the vertical channels 118 extend from a surface defining one of openings 122, 124, described in greater detail below, to one of superior surface 110 and inferior surface 112, as shown in FIG. 1A. Finally, a third group of channels 117 extend in a leading-trailing axis from leading surface 104 to central opening 113, as shown in FIG. 1B. Channels 117 may also be equally spaced from one another although as a group, as with the other channels, any pattern for the channels is contemplated. Additionally, channels may have varied spacing to fit around openings and other structural features of the implant body. The channels in the implant promote improved bone ingrowth and bone ongrowth. Further, inclusion of channels through the implant provides improved visualization through the implant both in person and via X-ray. For example, visualization is improved compared to solid titanium.

Turning to the operative openings defining implant 100, i.e., openings for bone fasteners and the locking element, the implant also includes a central opening 113 that extends through the implant from the superior surface to the inferior surface, as shown in FIG. 1B. Central opening 113 is irregularly shaped, though an exact shape of the central opening may be different in alternative arrangements to accommodate particular surgical applications. The implant also includes a series of surfaces recessed from trailing surface 102 and leading to central longitudinal opening 111. In turn, central longitudinal opening 111 is a passage extending an entirety of a distance between trailing surface 102 and central opening 113. Central longitudinal opening 111 is centered coincident with a central longitudinal axis 182 of implant 100 and is sized for disposal of locking element 150 therein. As shown in FIG. 1B, central longitudinal axis 182 is midway between side surfaces 106, 108.

Figure 1D:
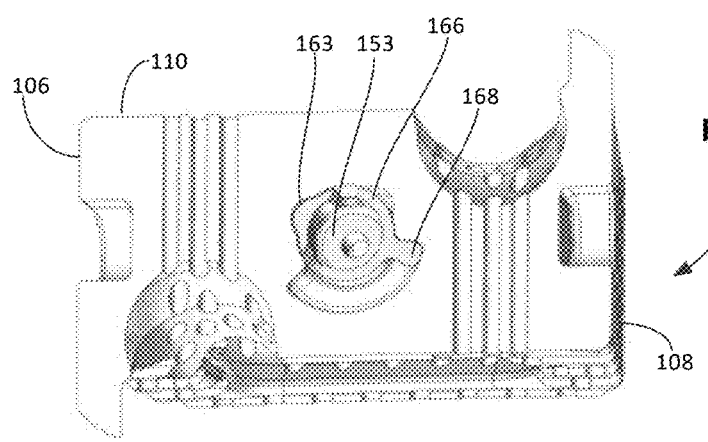
FIG. 1D is a sectional view of the implant and locking element of FIG. 1A.
Figure 1E:
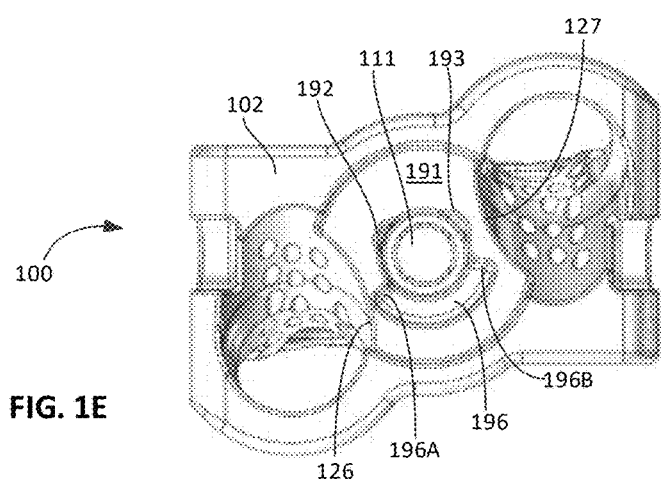
FIG. 1E is a sectional view of the implant of FIG. 1A.

Turning to the details of the recessed surfaces, FIG. 1E illustrates the trailing surface of the implant without the locking element. Immediately internal to trailing surface 102 is recessed surface 191, the recessed surface having an arcuate perimeter in superior and inferior directions and following a path of openings 122, 124 on sides separating the superior and inferior sides. The perimeter of recessed surface 191 is shaped to follow a footprint of the locking element through its range of rotational movement on the surface. This principle similarly applies to many of the other implants described herein. A depth of recessed surface 191 is sufficient so that head 152 of locking element 150 may be disposed therein. Within recessed surface 191 is opening 111, with additional recessed areas extending outward from opening 111 immediately below recessed surface 191. In particular, on one side of opening are indentations 192, 193, spaced apart from one another. On an opposite side is groove 196 with a surface that extends circumferentially around part of opening 111 from a first end 196A to a second end 196B. The above described surface features are sized and positioned to receive complementary features on locking element 150. In particular, and as shown in FIG. 1D, protrusion 163 of locking element is disposable in either indentation 192, 193 and movable between the two by rotation of locking element 150 when the locking element is in the implant. Upper protrusion 168 slides within groove 196 between its ends 196A-B. Details of locking element 150 are described below.

Further to central longitudinal opening 111, trailing surface 102 of the implant also includes two additional openings 122, 124, each located peripherally relative to central longitudinal opening 111, as shown in FIGS. 1A and 1E. These openings are also interchangeably referred to as passageways throughout the disclosure. Each opening 122, 124 extends into a body of the implant at an angle relative to a transverse plane 184 through the implant, as shown in FIGS. 1A and 1C. Transverse plane 184 is a central plane through the implant that is located in between the superior and the inferior surface. More specifically, a vector representing a central path of opening 122 from the trailing surface into the body of the implant is in an inferior direction away from transverse plane 184, while a vector representing a central path of opening 124 from the trailing surface of the body into the body of the implant is in a superior direction away from transverse plane 184. In this manner, openings 122, 124 are angled in opposite directions relative to transverse plane 184. Each opening 122, 124 may be angled from approximately 25 to 45 degrees relative to transverse plane 184 when the locking element is disposed in the implant. Thus, an angle between a central axis through opening 122 and a central axis through opening 124 may be in a range from 50 degrees to 90 degrees. In some examples, each opening 122, 124 is equal and opposite. For instance, each opening 122, 124 may be angled at 35 degrees relative to transverse plane 184 for a total angle of 70 degrees between central axes of openings 122, 124. In other examples, one opening is at a 35 degree angle relative to transverse plane 184. In at least some examples, each opening sized for fastener placement is parallel to the other when viewed in the transverse plane. Put another way, the openings remain at the same lateral distance from central longitudinal axis 182 over their length. The location of openings 122, 124 on the implant and their associated angulation is advantageous in that it allows for fasteners disposed in the openings to engage a vertebra near one of its corners when the implant is disposed in an intervertebral space.

Trailing surface 102 also includes notches 138A-B on opposite sides of trailing surface 102 at side surfaces 106, 108, respectively. Each notch 138A-B is approximately aligned with transverse plane 184. Notches 138A-B are sized for engagement by a tool, such as an insertion instrument, described in greater detail elsewhere in the present disclosure.

To accommodate the advantageous location and angulation of openings 122, 124 within implant 100, implant 100 includes ridges 132, 134 that protrude relative to other more planar surfaces of the implant. In light of the opposite direction of respective openings 122, 124, ridge 132 extends outward from inferior surface 112 while ridge 134 extends outward from superior surface 110. Each ridge 132, 134 defines part of the respective opening 122, 124 entry on trailing surface 102. As shown in FIG. 1A, each ridge 132, 134 is arcuate in shape with a concave surface facing inward toward a respective opening. The concave inside surface of each ridge 132, 134 is angled to align with a pathway of a respective opening. For example, the inside surface of ridges 132, 134 may define a partially cylindrical shape with a center becoming further from transverse plane 184 at locations of the implant further from trailing surface 102. In another example, when opening 122 is angled at 35 degrees relative to transverse plane 184, then a superior apex of the inner surface of ridge 132 may be at a 35 degree angle relative to the transverse plane. Each ridge 132, 134 is shallow in depth and recedes to the primary superior and inferior surfaces 110, 112, close to trailing surface 102, as shown in FIG. 1C. The inclusion of ridges 132, 134 on the implant provides geometry to allow for screw trajectories to place screws into corners of the adjacent vertebral bodies. By anchoring screws into corners of the adjacent vertebral bodies, bone purchase and stability is optimized. Additionally, ridges 132, 134 may provide a stop surface to abut against vertebral bodies when the implant is positioned in an intervertebral space. Also on trailing surface 102, immediately superior and inferior to central longitudinal opening 111 are respective secondary protrusions 132A, 134A that define convex external surfaces. As shown in FIG. 1A, the curvature of these protrusions is approximately parallel to that of a head of locking element 150.

Figure 1F:
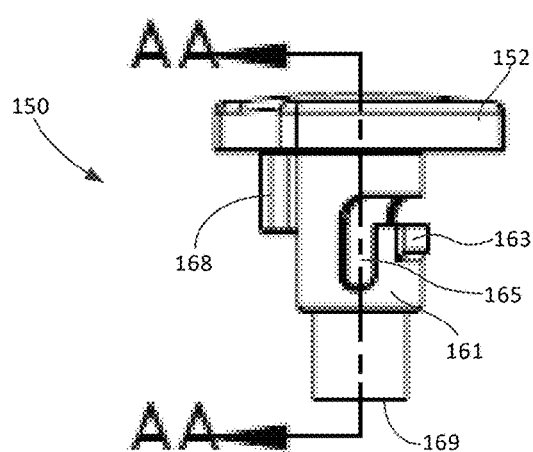
FIGS. 1F-1G are views of the locking element of FIG. 1A.
Figure 1G:
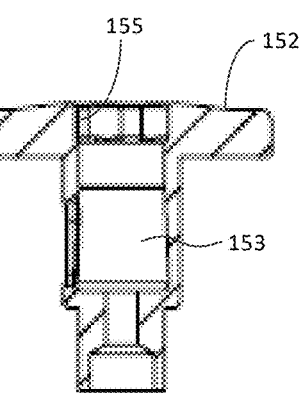

Turning to the details of locking element 150, the features of locking element 150 are best shown in FIGS. 1F and 1G. In particular, locking element 150 includes a head 152 and a shaft 166 extending from one side of the head to a free end 169. Inside locking element 150 is a cavity 153 that extends through head 152 and into shaft 166. The cavity is oriented and sized to accommodate receipt of a portion of a tool, such as insertion instrument 1300, described in greater detail elsewhere in the present disclosure. At the entrance into cavity 153 at the head is a drive element 155 shaped to receive a driver (not shown) for actuation of the locking element. The driver may be a screw driver or other similar tool. Shaft 166 includes an open volume 165 that is carved out of part of a cylindrical surface of shaft 166. Open volume 165 is partially enclosed by a flexible bar 161. Flexible bar 161 extends from a first end at a base of open volume 165 and opposite a main portion of shaft 166, to a second, free end closer to head 152, as shown in FIG. 1F. At the free end of flexible bar 161 is a protrusion 163 extending outward from flexible bar 161. The inclusion of flexible bar 161 with protrusion 163 allows for locking element 150 to be rotated between at least two locked positions in the implant. For instance, to move from a first locked position to a second locked position, flexible bar 161 of locking element 150 is adapted to flex inward toward shaft 166 to bring protrusion 163 out of a first engagement feature, e.g., indentation 192, within central longitudinal opening 111 of the implant, and locking element 150 is further adapted to be rotatable so that protrusion 163 may be rotated into a second engagement feature, e.g., indentation 193, within central longitudinal opening 111. In one position, head 152 of locking element 150 may partially block openings 122, 124. In another position, openings 122, 124 may be unimpeded. In this and many other implant embodiments, rotational adjustment of the locking element is accompanied by visual, audible and tactile feedback to signal a change in a position of the locking element on or in the implant. The above described structural characteristics are described in greater detail in the method of use embodiments of the present disclosure.

Locking element 150 also includes upper protrusion 168, shown in FIG. 1F, directly abutting head 152 and extending outward from shaft 166. Upper protrusion 168 is adapted to be disposed in groove 196, an arcuate-shaped recess in implant 100, when locking element 150 is disposed in the implant. In particular, groove 196, within recessed surface 191, has an elongate dimension that limits a range of rotation of upper protrusion 168 by blocking its rotation beyond ends 196A, 196B of the arcuate shaped groove. In this manner, an overall rotation of locking element 150 is limited to a predetermined range.

In one embodiment, an implant 200 and complementary locking element 250 are as shown in FIGS. 2A-2F. For implant 200, unless otherwise noted, like reference numerals refer to like elements of implant 100, but within the 200 series of numbers. Implant 200 has generally the same outer shape as implant 100, though central opening 213 is a different shape.

Figure 2B:
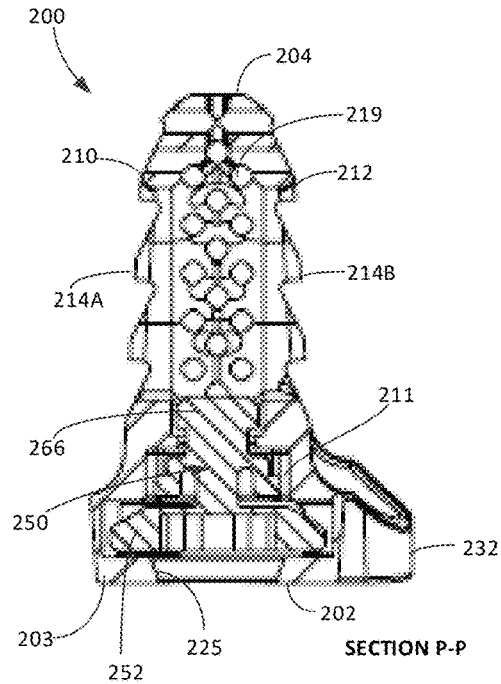
Figure 2C:
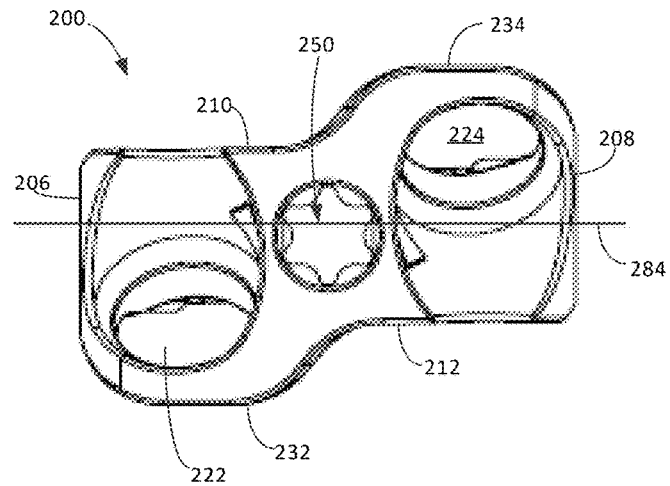

In contrast with implant 100, locking element 250 for implant 200 is disposed within an internal cavity 211 so that locking element 250 is not removable from the implant 200 after the implant is formed, a process described elsewhere in the present disclosure, e.g., ALM implant formation. The location of locking element 250 within implant 200 is best shown in FIG. 2B. Beginning with the surface features of the implant surrounding internal cavity 211, drive element 255 of the locking element is accessible from trailing surface 202 via a trailing access 225. Trailing access 225 is an opening into cavity 211 that is aligned with a longitudinal axis 282, although access 225 is smaller than head 252 of locking element 250, thereby preventing locking element 250 from dislodging from implant 200 on the trailing side of the implant.

Within cavity 211 is an outer part and an inner part. The outer part is defined by a volume between a trailing wall 203 on the trailing side of the implant and internal surface 291, as shown in FIGS. 2B and 2D. The volume of the outer part of cavity is sized for the rotatable disposal of head 252 of implant 200 therein. Superior and inferior sides of surface 291 are generally arcuate, though each opposing side includes a protrusion 288, 289, respectively, sized and positioned to prevent over-rotation of locking element 250. Between the opposing superior and inferior sides of surface 291 are openings in the form of side accesses 226, 227, or slots, that place cavity 211 in direct communication with openings 222, 224. In this manner, locking element 250 may be rotatable so that part of the locking element structure enters the passageways through openings 222, 224. The inner part of cavity 211 is recessed and internal to internal surface 291. In particular, internal to surface 291 are four indentations of which two, 292A and 292B, are shown in FIG. 2D. The indentations are positioned at approximately equal angles with respect to one another as measured from axis 282, and are each sized for the disposal of one of protrusions 263A, 263B therein. In this manner, in any fixed rotational position of locking element 250 within implant 200, protrusions 263A, 263B occupy two of the four indentations.

Turning to locking element 250, shown in isolation in FIGS. 2E-2F, the locking element includes a head 252 and a shaft 266 extending from the head. Extending outward from the shaft on opposite sides are flexible bars 261A, 261B, separated from a main body of shaft 266 by open volumes 265A, 265B, respectively. Each flexible bar 261A, 261B is a cantilever and includes an exterior facing protrusion 263A, 263B at its respective free end. Protrusions 263A, 263B are sized for disposal in indentations 292A, 292B, and the other indentations internal to internal surface 291. Head 252 includes a first end portion 256 extending from a center of the locking element, i.e., at a center of drive element 255, and a second end portion 258 also extending from drive element 255, but in an opposite direction. Each end portion is offset from a superior-inferior axis centerline of locking element 250, though portion 256 is offset in a first direction while portion 258 is offset in a second, opposite direction. This is best shown in FIGS. 2D and 2F. One advantage derived from the housing of locking element 250 internally within cavity 211 is that locking element 250 is prevented from dislodging from the implant through the trailing face of the implant.

In one embodiment, implant 300 and complementary locking element 350 are as shown in FIGS. 3A-3G. For implant 300, unless otherwise noted, like reference numerals refer to like elements of implant 200, but within the 300 series of numbers. In instances where the elements for implant 200 are not described, like reference numerals refer to like elements of implant 100, but within the 300 series of numbers.

Figure 3A:
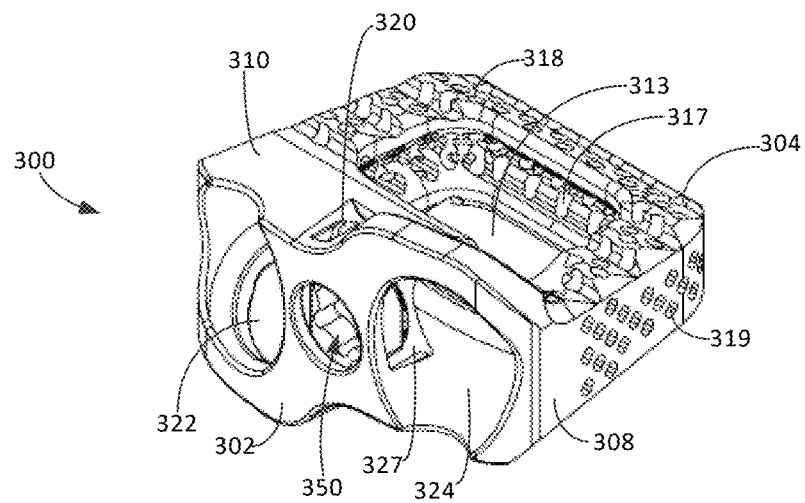
FIGS. 3A-3C are various views of an implant with a locking element disposed therein according to another embodiment of the disclosure.
Figure 3B:
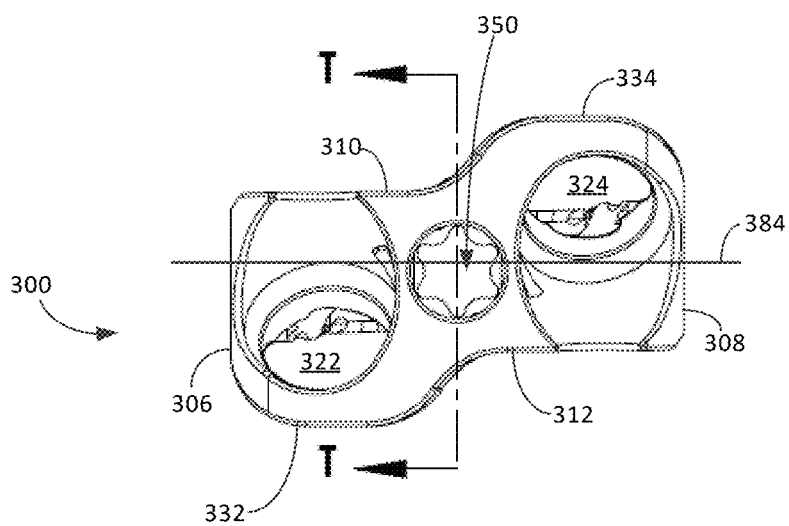
Figure 3C:
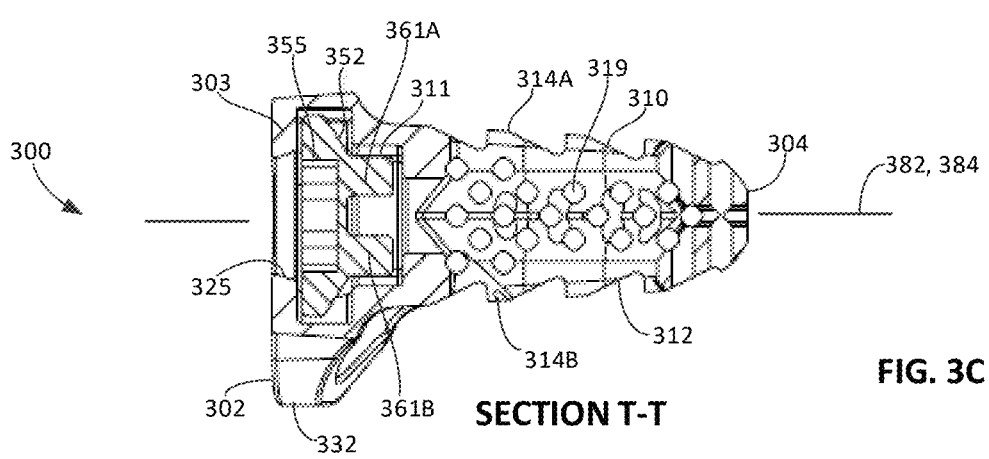
Figure 3D:
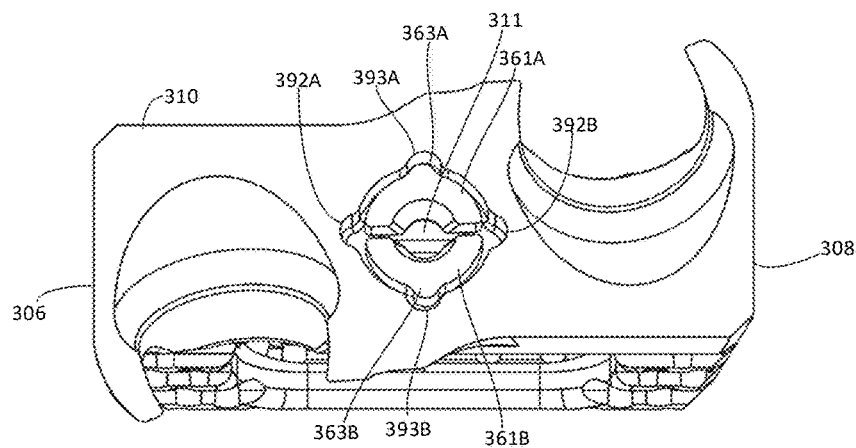
FIGS. 3D-3E are sectional views of the implant and locking element of FIG. 3A.
Figure 3E:
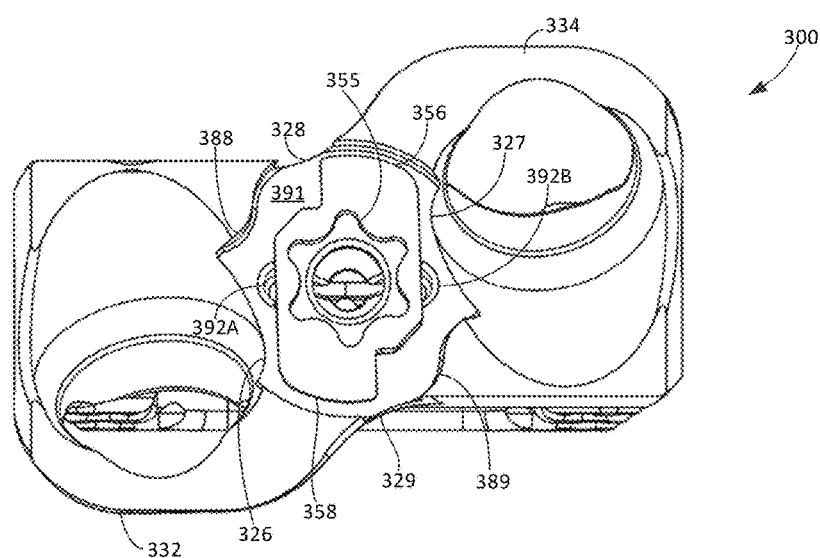

Turning initially to the structure sized for disposal of locking element 350 within implant 300, implant includes an inner cavity 311 with an outer part defined between a trailing wall 303 and surface 391 within implant 300, as shown in FIGS. 3C and 3E, and an inner part recessed relative to surface 391. The outer part is bounded by four separate and generally arcuate shaped walls, as shown in FIG. 3E, each wall separated from the other by accesses 326, 327, 328, 329. Side accesses 326, 327 provide for direct communication between inner cavity 311 and openings 322, 324 while superior and inferior accesses 328, 329 provide for direct communication with a superior side and an inferior side of the implant, respectively. Two of the walls defining outer part of inner cavity 311 oppose one another and include protrusions 388, 389, respectively, sized and positioned to limit rotational movement of locking element 350. Interior to internal surface 391 are indentations 392A-D, best shown in FIG. 3D. Each indentation extends internal relative to surface 391 as part of inner cavity 311.

Figure 3F:
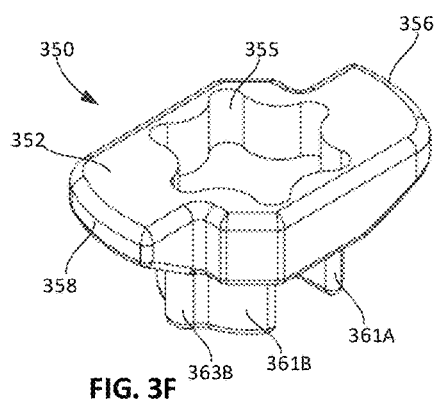
FIGS. 3F-3G are views of the locking element of FIG. 3A.
Figure 3G:
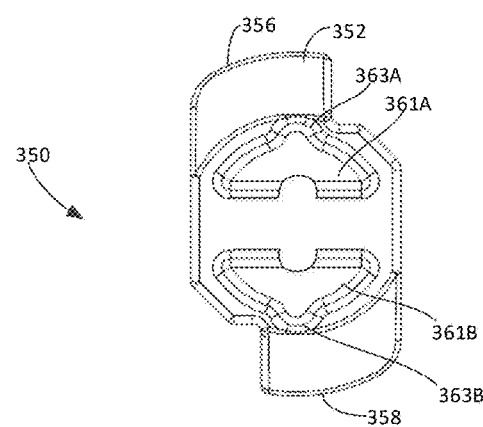

Locking element 350, shown in isolation in FIGS. 3F and 3G, is sized for disposal within implant 300 and is formed together with implant, e.g., via ALM, so that it is not detachable once the combined structure is formed. Locking element 350 includes head 352 and two flexible bars 361A, 361B extending therefrom. Each flexible bar is a mirror opposite of the other, as shown in FIGS. 3D and 3G. With reference to one flexible bar as representative, flexible bar 361A has an arcuate shape that is relatively uniform along its length as measured in a longitudinal axis of the locking element. On an internally facing surface of flexible bar 361A is a concave curved recess, thereby providing a pathway through the implant from trailing surface 302 to central opening 313 even with locking element 350 disposed in the implant. On a central externally facing surface of flexible bar 361A is a protrusion 363A. Head 352 is sized for disposal in outer part of internal cavity 311 while protrusions 363A. 363B are each sized to snap-fit into any one of indentations 392A-B, 393A-B, a position of the locking element being adjustable through rotation of locking element within the internal cavity. One locked position of locking element 350 within implant 300 is illustrated in FIG. 3D.

In one embodiment, implant 400 and complementary locking element 450 are as shown in FIGS. 4A-4E. For implant 400, unless otherwise noted, like reference numerals refer to like elements of implant 200, but within the 400 series of numbers. In instances where the elements for implant 200 are not described, like reference numerals refer to like elements of implant 100, but within the 400 series of numbers.

As with implant 200 and 300, locking element 450 is entirely disposed within implant 400 in a manner such that locking element 450 is held within an internal cavity 411. Turning to the structure of the internal cavity, internal to internal surface 491 is an inner part of internal cavity 411, shown in section in FIG. 4D. The inner part is defined by a perimeter punctuated by protrusions 497B, 497D. Outer and inner parts of internal cavity 411 are sized for the disposal of head 452 and shaft 466 of locking element 450, respectively.

Figure 4A:
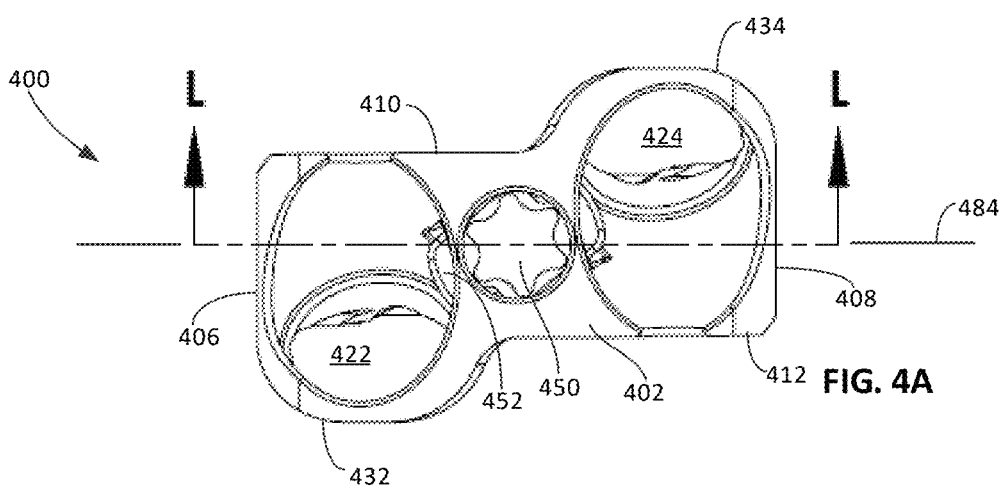
FIGS. 4A-4C are various views of an implant with a locking element disposed therein according to another embodiment of the disclosure.
Figure 4B:
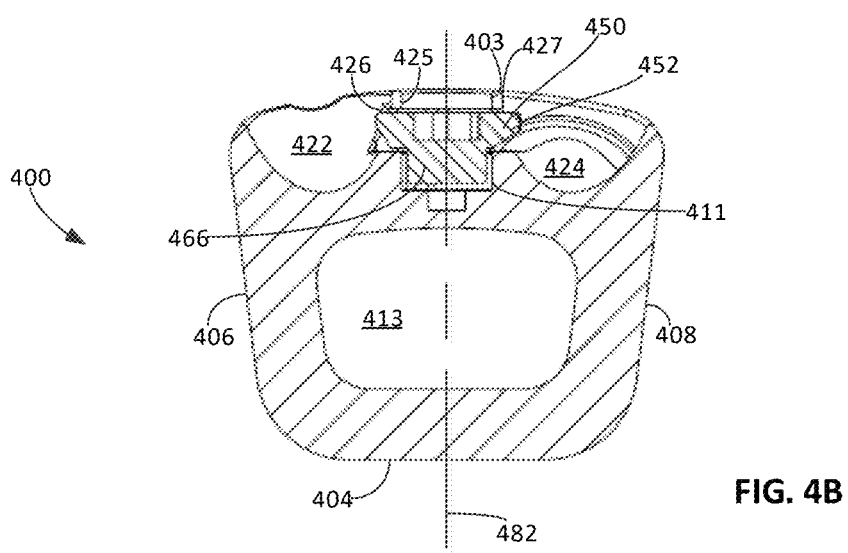
Figure 4C:
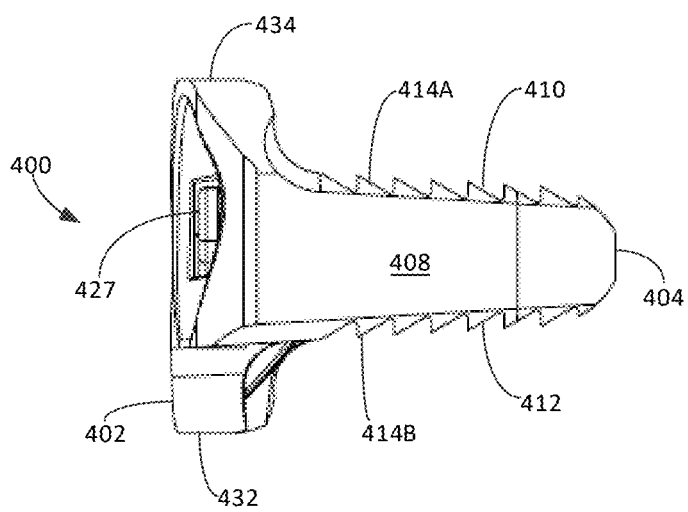
Figure 4D:
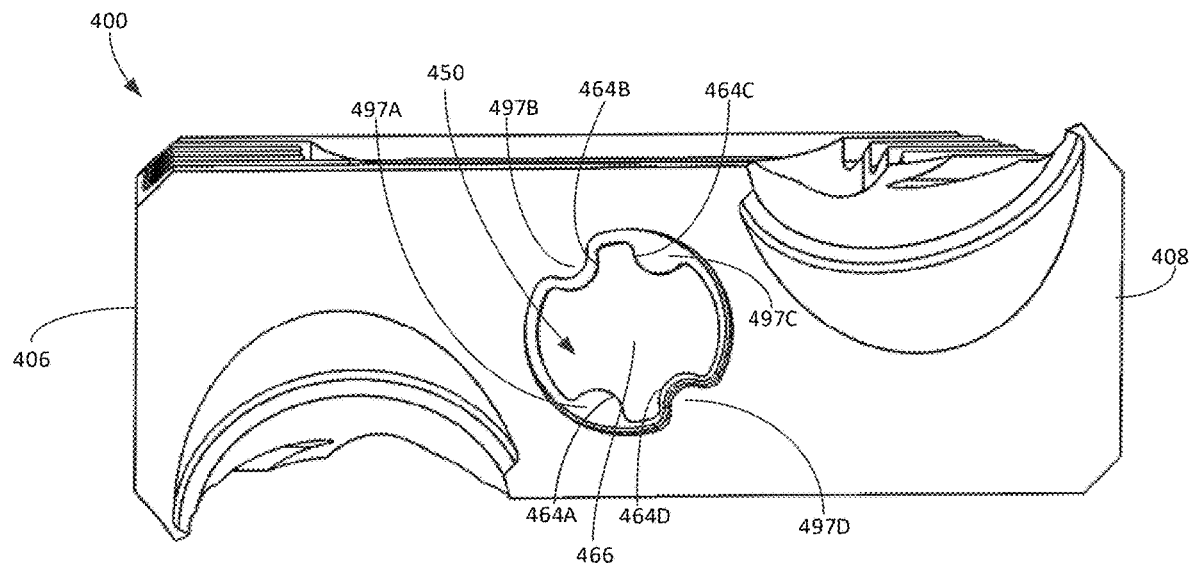
FIGS. 4D-4E are sectional views of the implant and locking element of FIG. 4A.
Figure 4E:
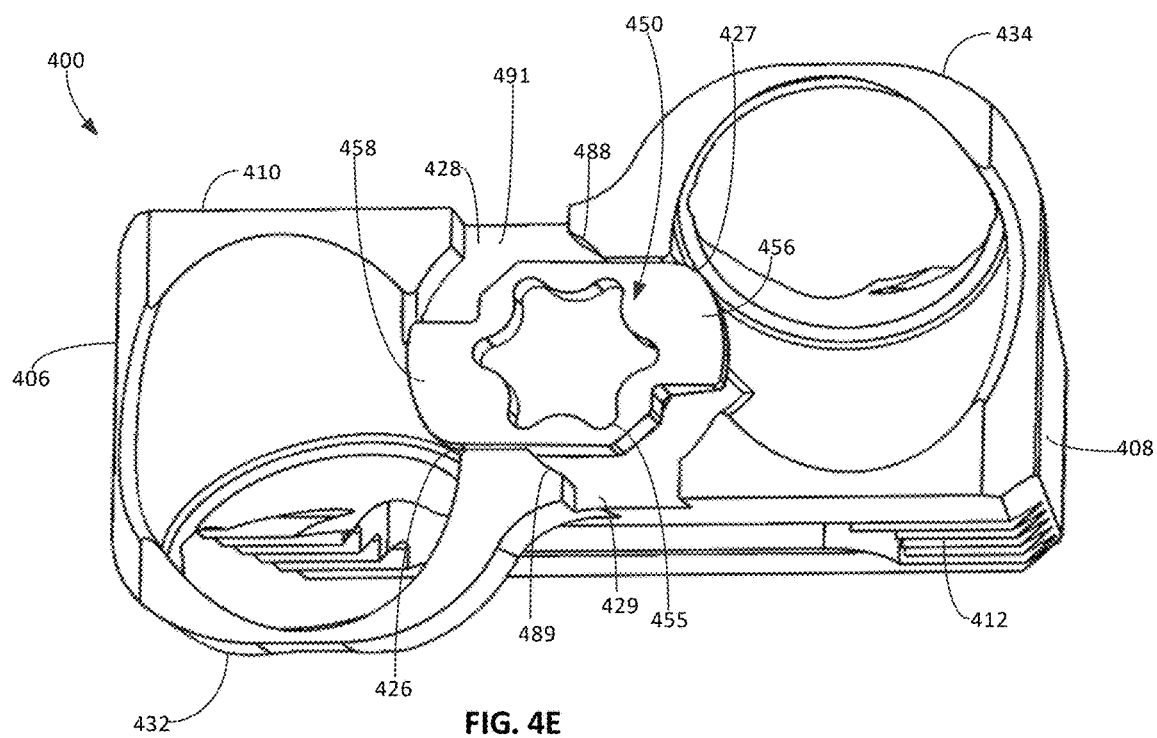

Locking element 450 includes head 452 and shaft 466 extending therefrom, as shown in FIG. 4B. Shaft 466 is a solid body with a partially cylindrical shape extending along a length from the head. The shaft includes troughs 464A-D, each oriented in a lengthwise manner and spaced apart from the others. The geometry of the internal cavity 411 and locking element 450 are complementary such that locking element 450 is rotatable within the cavity into more than one locked setting whereby a trough, e.g., 464A, may be moved from being unengaged with a protrusion to being engaged with protrusion 497D. Such adjustments change an orientation of head 452 between a first orientation shown in FIG. 4E, where head 452 is blocking openings 422, 424, and a second orientation where head 452 is entirely over interior surface 491 and no longer blocks either opening 422, 424.

In one embodiment, implant 500 and complementary locking element 550 are as shown in FIGS. 5A-5E. For implant 500, unless otherwise noted, like reference numerals refer to like elements of implant 100, but within the 500 series of numbers. In instances where the elements for implant 200 are not described, like reference numerals refer to like elements of implant 100, but within the 500 series of numbers.

In implant 500, ridges 532, 534 are reversed relative to the ridges of implant 100 so that ridge 532 protrudes on superior surface 510 while ridge 534 protrudes on inferior surface 512. This configuration is commensurate with opening 522 being angled in a superior direction from the trailing end toward the leading end of the implant while opening 524 is angled in an inferior direction from the trailing end toward the leading end.

Figure 5D:
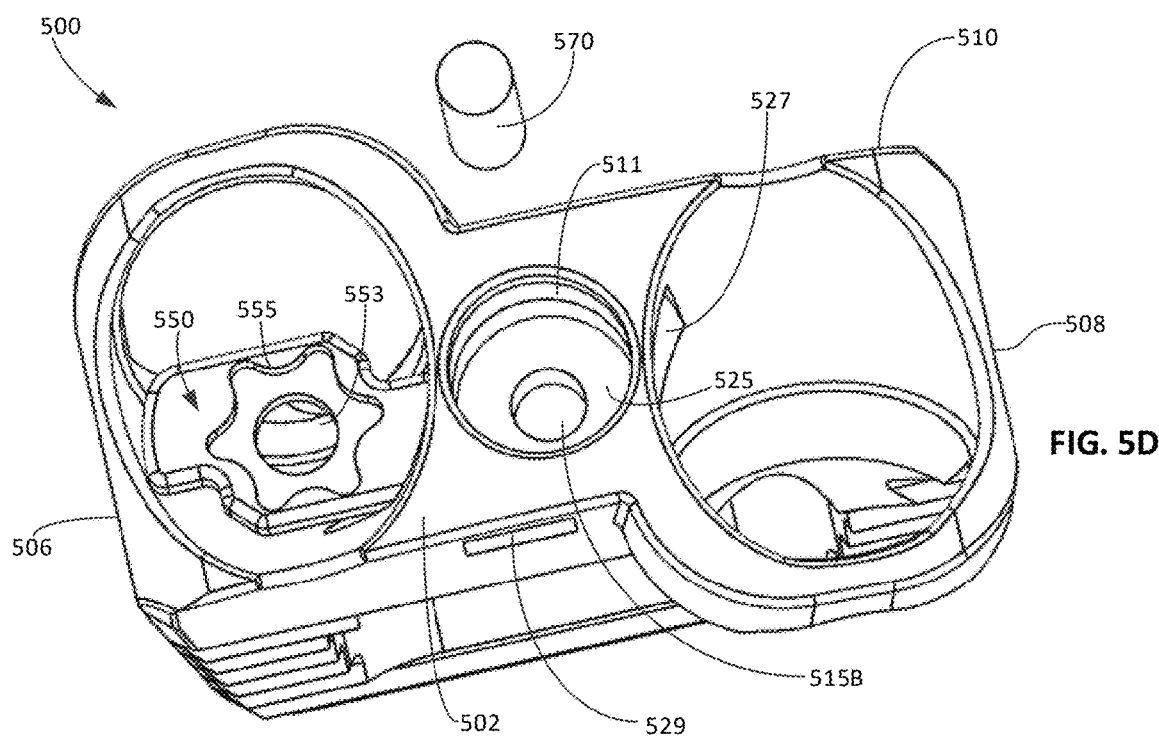
FIG. 5D is a perspective view of the implant and locking element of FIG. 5A during assembly.
Figure 5E:
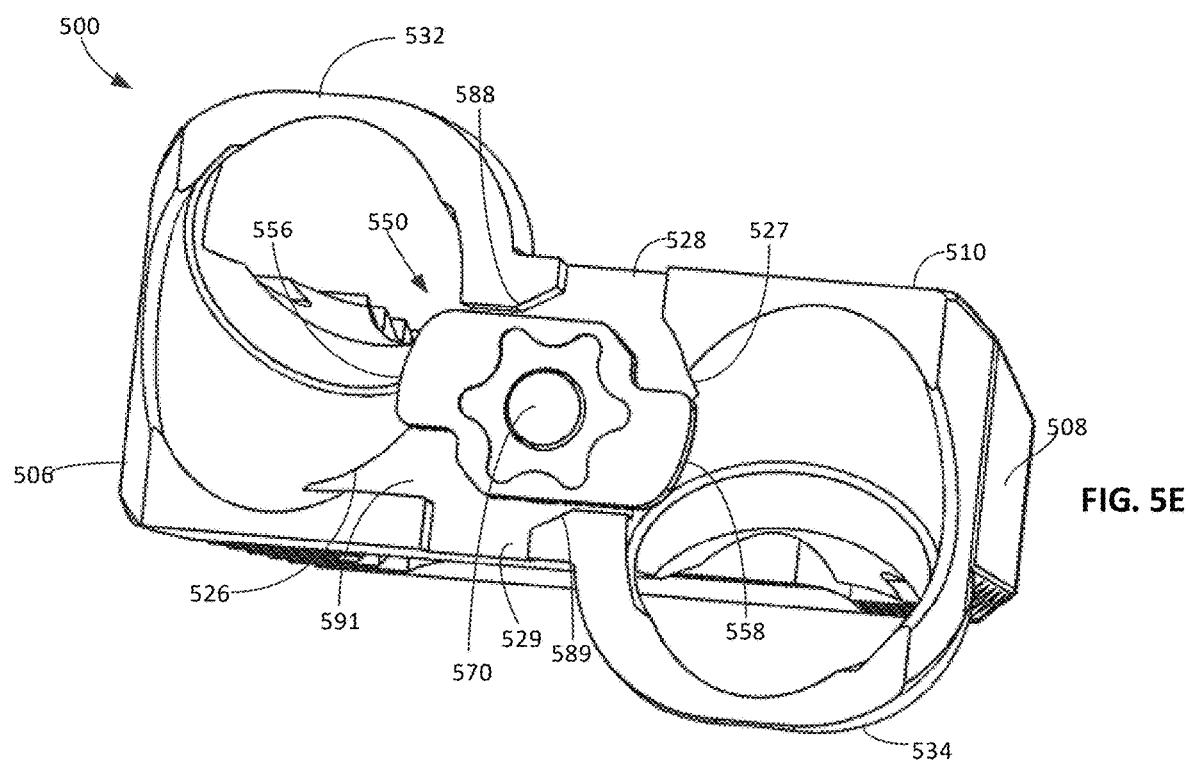
FIG. 5E is a sectional view of the implant and locking element of FIG. 5A.

Implant 500 includes an internal cavity 511 with an outer part sized to house locking element 550 and an inner part sized to receive pin 570, as shown in FIGS. 5B and 5D. From trailing surface 502, trailing access 525 through trailing wall 503 connects the trailing surface of the implant to internal cavity 511. The outer part of internal cavity 511 extends between wall 503 and internal surface 591, and is bounded between openings 522, 524 by four side walls each separated by two of accesses 526, 527, 528, 529, as shown in FIG. 5E. Side accesses 526, 527 provide space to allow ends of locking element 550 to rotate into openings 522, 524, while superior and inferior accesses 528, 529 connect exterior surfaces of the implant with the internal cavity. Continuing to refer to the outer part of internal cavity, protrusions 588, 589 provide a blocking surface that limits the extent to which locking element 550 is rotatable within the implant. Interior to internal surface 591 is inner part of internal cavity 511 including a second recessed volume 515A and a third recessed volume 515B, shown in FIGS. 5B and 5D. In variants, recessed volume 515B may directly communicate with internal cavity 511 without a second recessed volume. In this manner, pin 570 may be entirely enclosed within recessed volume 515B below internal cavity 511. As shown in FIG. 5B, the internal cavity, as a whole, is sized to accommodate disposal of locking element 550 and pin 570 therein, where pin is disposed through locking element 550 and into third recessed volume 515B. The pin and internal cavity are both shaped and surfaced so that pin 570 engages walls within third recessed volume 515B through an interference fit.

Locking element 550 is best shown in FIGS. 5D and 5E and includes end portions 556, 558, a central drive element 555, and a central opening 553 through the drive element. Locking element 550 does not include a shaft. Rather, opening 553 is sized for the disposal of a pin 570 therein, as shown in FIG. 5B. Additionally, side accesses 526, 527, or slots, in implant 500 are sized and positioned within respective openings 522, 524 such that locking element 550 is insertable into cavity 511 by sliding it into one of side accesses 526, 527, as shown in FIG. 5D. In this manner, locking element 550, complemented by pin 570, is advantageous in that it can be inserted into a formed implant even when the implant otherwise prevents disengagement of a locking element through trailing surface 502. It should be appreciated that the assembly of locking element 550 with implant 500 takes place during manufacture.

In one embodiment, implant 600 and complementary locking element 650 are as shown in FIGS. 6A-6E. For implant 600, unless otherwise noted, like reference numerals refer to like elements of implant 200, but within the 600 series of numbers. In instances where the elements for implant 200 are not described, like reference numerals refer to like elements of implant 100, but within the 600 series of numbers. Additionally, it should be appreciated that ridges 632, 634 are reversed relative to the ridges of implant 100, but that the ridge structures are otherwise the same as those described for implant 100 or contemplated alternatives.

Figure 6A:
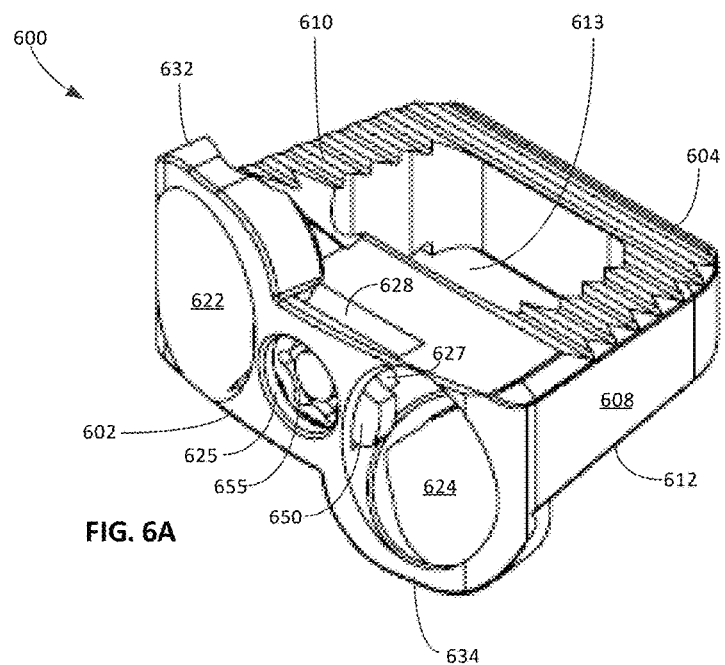
FIGS. 6A-6C are various views of an implant with a locking element disposed therein according to another embodiment of the disclosure.
Figure 6B:
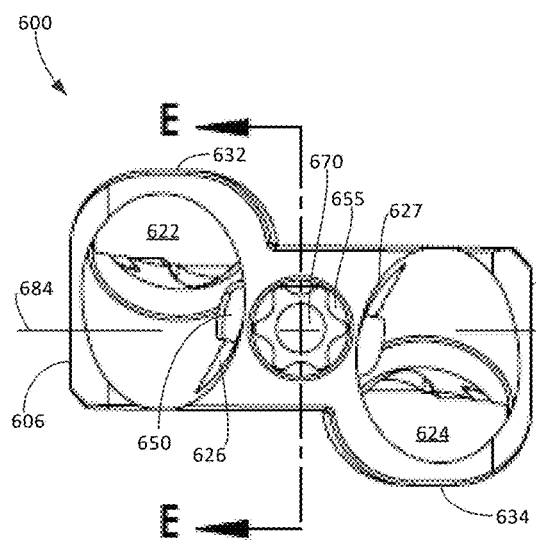
Figure 6C:
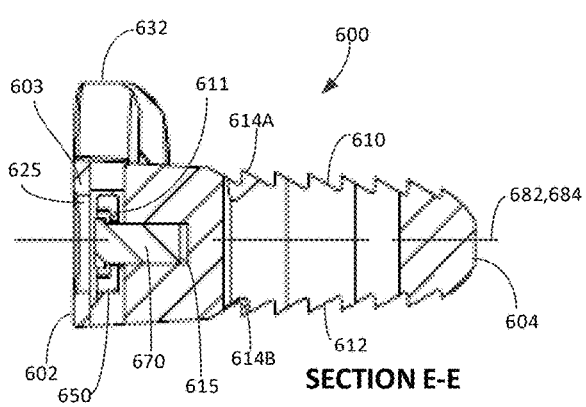
Figure 6D:
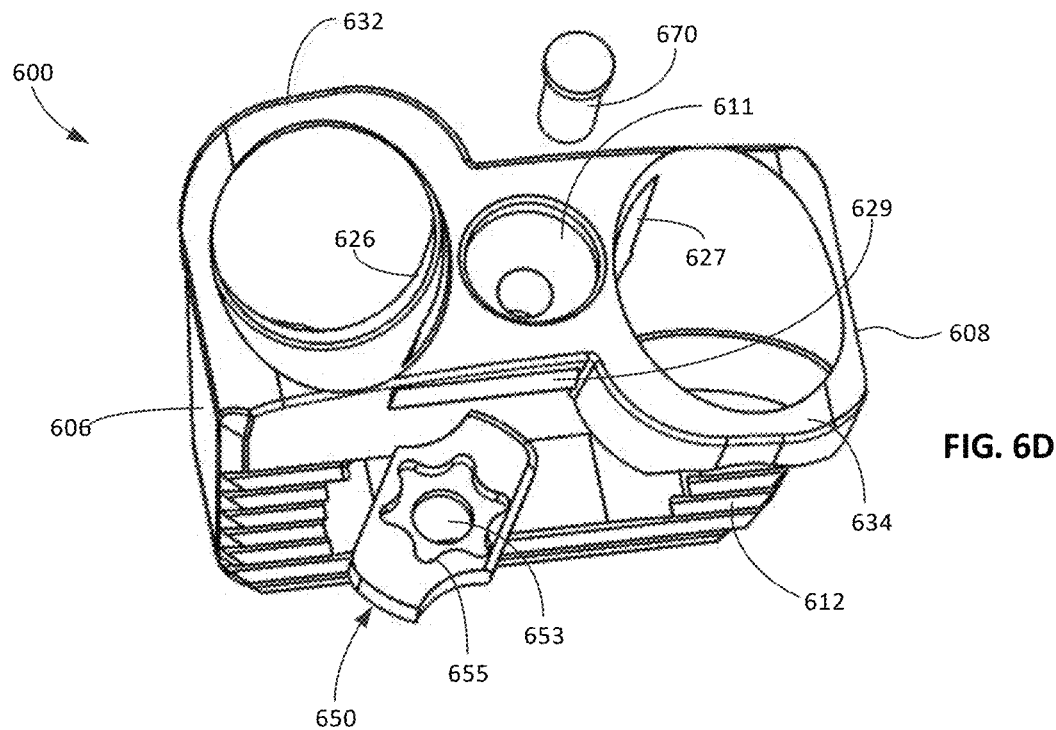
FIG. 6D is a perspective view of the implant and locking element of FIG. 6A during assembly.
Figure 6E:
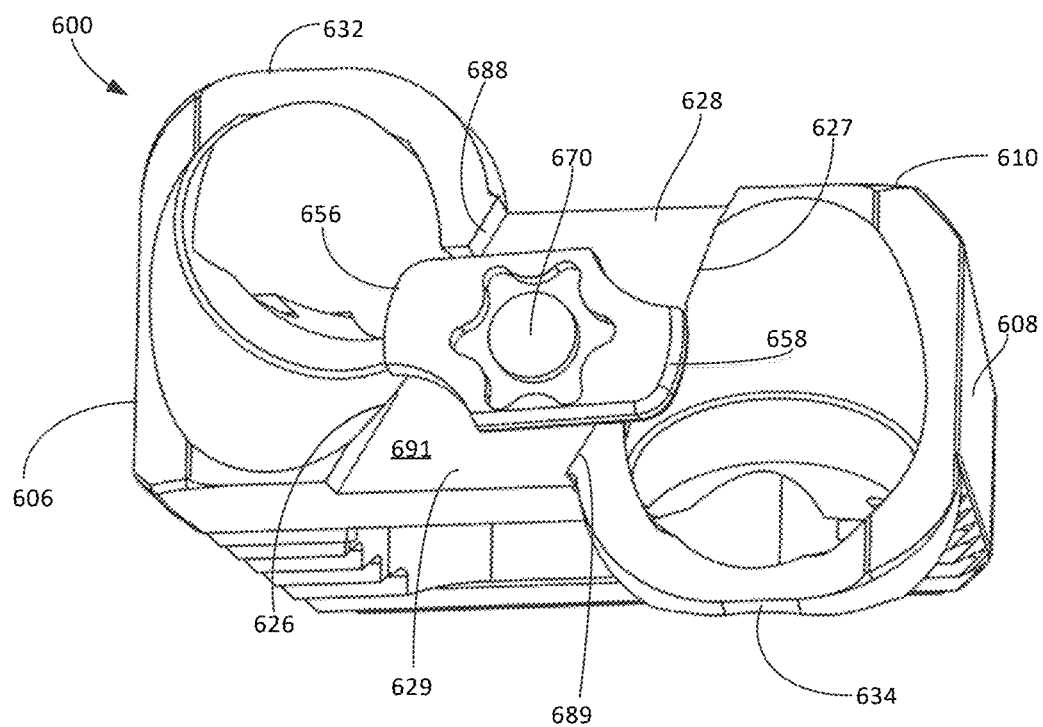
FIG. 6E is a sectional view of the implant and locking element of FIG. 6A.

As with implant 500, implant 600 includes an interior cavity 611 in communication with trailing surface 602 via trailing access 625. Within interior cavity 611 is an outer part between wall 603 and internal surface 691 and an inner part within recessed volume 615. A volume of upper part is defined by parallel walls that are diagonal to side surfaces 606, 608 of implant 600, as shown in FIG. 6E, and includes blocking protrusions 688, 689 to prevent over-rotation of locking element 650. Outer part of interior cavity 611 is in communication with four access regions, i.e. slots, including side accesses 626, 627, superior access 628 and inferior access 629. Each access 626, 627, 628, 629 is fully enclosed on all sides and has dimensions sufficient so that locking element 650 may be slid from outside of the implant into cavity 611 via either opening 622, 624 or via superior or inferior surfaces 610, 612. For example, in FIG. 6D, locking element 650 is shown as ready for insertion through inferior access 629. It should be appreciated that in alternative arrangements, the implant may include any sub combination of the four described access slots. For instance, three access openings in total: one on the superior surface and one in each fastener opening.

In FIG. 6E, the outer part of interior cavity 611 is sized to house locking element 650 with a pin 670 disposed therein, the pin further extending into recessed volume 615. Locking element includes a drive element 655 and an opening 653 through the drive element, the opening at a center of the locking element and sized for receipt of pin 670. As shown in FIG. 6D, pin includes a lip, though pin may have alternative surface features chosen to suit the interconnectivity between the pin and the locking element. Pin 670 disposed in locking element 650 within implant 600 is shown in FIG. 6E. Locking element 650 is held in position within implant 600 by pin 670, which maintains an orientation of the locking element relative to the implant. Pin 670 is held fixed via an interference fit, i.e., press or friction fit, between pin 670 and walls of recessed volume 615, although it is contemplated that other forms of interconnection between the pin and the implant may also be employed. As with implant 500, locking element 650 is formed within or placed in implant 600 during manufacture.

In one embodiment, implant 700 and complementary locking element 750 are as shown in FIGS. 7A-7E. For implant 700, unless otherwise noted, like reference numerals refer to like elements of implant 300, but within the 700 series of numbers. In instances where the elements for implant 200 are not described, like reference numerals refer to like elements of implant 100, but within the 700 series of numbers. Additionally, it should be appreciated that ridges 732, 734 are reversed relative to the ridges of implant 100, but that the ridge structures are otherwise the same as those described for implant 100 or contemplated alternatives.

Figure 7D:
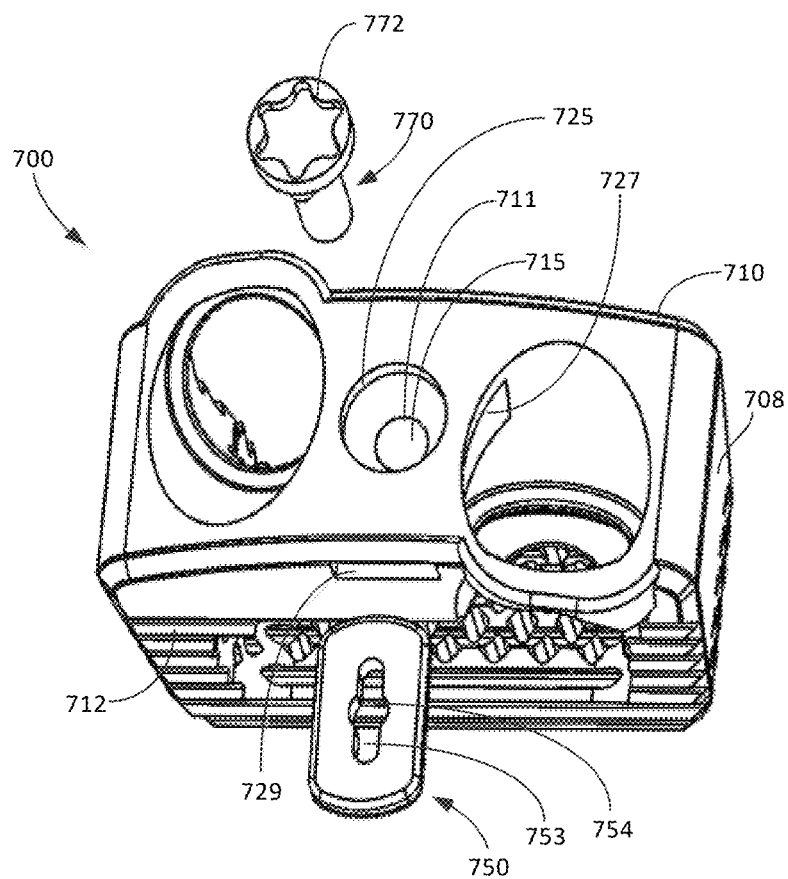
FIG. 7D is a perspective view of the implant and locking element of FIG. 7A during assembly.
Figure 7E:
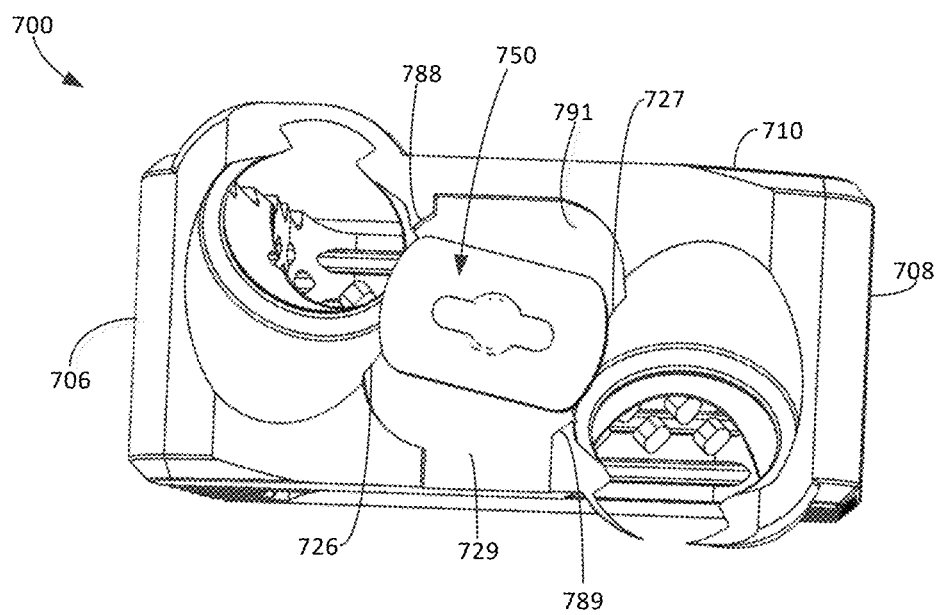
FIG. 7E is a sectional view of the implant and locking element of FIG. 7A.

As with implant 500, implant 700 includes an interior cavity 711 in communication with trailing surface 702 via trailing access 725. Within interior cavity 711 is an outer part between trailing wall 703 and internal surface 791 and an inner part corresponding to recessed volume 715. As shown in FIG. 7E, a volume of upper part is defined by three walls, one on a superior side of the upper part, another on a side facing opening 722, and a third on a side facing opening 724. The second and third walls are separated by inferior access 729, while the first wall of the outer part is separated from the other walls by side accesses 726, 727. Each access 726, 727, 729 is a fully enclosed on all sides. The first wall and the third wall include blocking protrusions 788, 789, respectively, to prevent over-rotation of locking element 750, when disposed in the implant. As noted above, outer part of interior cavity 711 is in communication with three access regions, including side accesses 726, 727 and inferior access 729. Access 729 has dimensions sufficient so that locking element 750 may be slid from outside of the implant into cavity 711. In FIG. 7D, locking element 750 is shown as ready for insertion through inferior access 729. It should be appreciated that in alternative arrangements, implant 700 may also include an access opening from the superior surface in addition to or as a substitute for inferior access 729.

As shown in FIGS. 7C and 7E, the outer part of interior cavity 711 is sized to house locking element 750 with a pin 770 disposed therein, the pin also extending further into an inner part of interior cavity 711, the inner part being recessed volume 715 that extends directly into central opening 713 of implant. Locking element 750 includes an elongate slot 753 through its central axis with a widened opening 754 at its center, as shown in FIG. 7D. Pin 770 includes a head with a drive element 772 therein. In this manner, when pin 770 is engaged with locking element 750, driving of the combined structure may be through the pin. Pin 770 also includes protrusions along its shaft, particularly immediately underneath the head, to hold pin rotationally fixed relative to locking element 750. In this manner, rotation of drive element 772 when pin is disposed in locking element causes the combined pin and locking element structure to rotate together. When disposed in implant 700, pin 770, disposed through locking element 750, is disposed within recessed volume 715 to form an interference fit with the implant body and locking element 750 is in turn held in place by pin. It should be appreciated that in alternative arrangements, other forms of interconnection between the pin and the implant may be employed. As with implant 500, locking element 750 is formed within or placed in implant 700 during manufacture.

In one embodiment, implant 800 and complementary locking element 850 are as shown in FIGS. 8A-8D. For implant 800, unless otherwise noted, like reference numerals refer to like elements of implant 100, but within the 800 series of numbers.

Figure 8A:
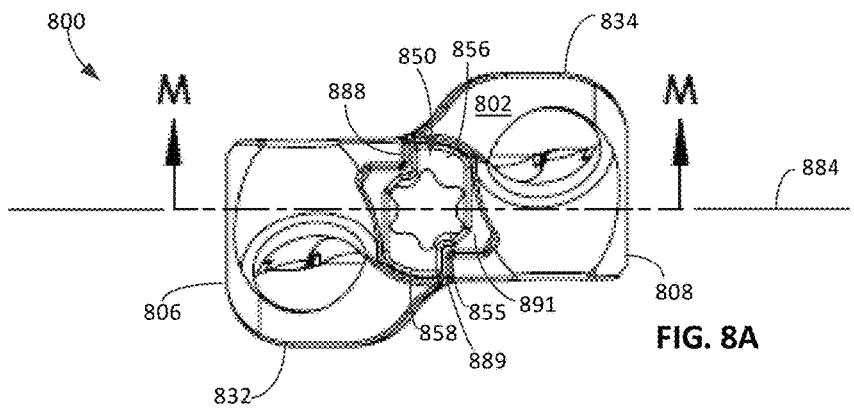
FIGS. 8A-8C are various views of an implant with a locking element disposed therein according to another embodiment of the disclosure.
Figure 8B:
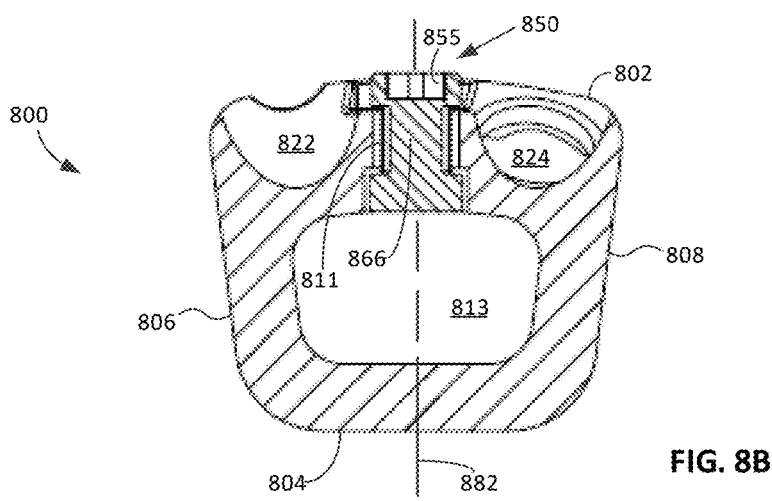
Figure 8C:
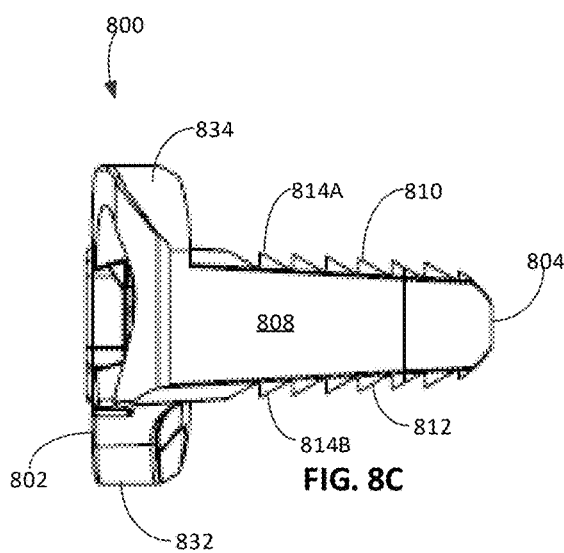

Implant 800 includes a recessed surface 891 for receipt of a head 852 of locking element 850, as shown in FIGS. 8A and 8B. Recessed surface 891 is shaped to accommodate rotation of locking element 850 when it is included therein, with protrusions 888, 889 extending inward closer to central axis 882 to limit the rotation of locking element. Interior to recessed surface 891 is central longitudinal opening 811, best shown in FIG. 8B, sized to accommodate disposal of a shaft of a locking element therein. Towards interior opening 813, central longitudinal opening 811 includes a wider portion to match a shape of shaft 866 of locking element, which is wider at opposite ends, as shown in FIG. 8B. Because the head 852 at one end and a distal shaft portion at an opposite end are both wider than a central portion of shaft 866, locking element is prevented from disengaging from implant 800 in both axial directions. A process of manufacturing implant 800 is similar to that utilized for implant 200, and is described in greater detail elsewhere in the disclosure.

Figure 8D:
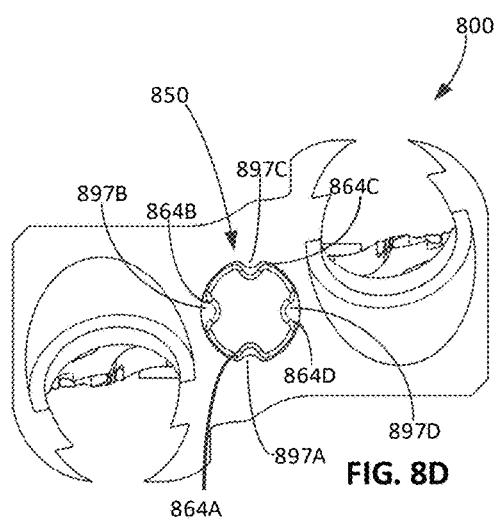
FIG. 8D is a perspective view of the implant and locking element of FIG. 8A during assembly.

Locking element 850 includes a head with offset end portions 856, 858 extending to ends of the locking element and a drive element 855 at its center longitudinal axis, as shown in FIG. 8A. Shaft 866 extends from the head and includes indents 864A-D similar to those described for implant 400. The indents on shaft 866 are sized and positioned so that locking element 850 may be rotatably fixed in different positions by moving an indentation into and out of one of protrusions 897A, 897C within central longitudinal opening 811. For example, indentation 864A may be moved from being on receiving protrusion 897A, as shown in FIG. 8D, to a position between protrusions 897A, 897C in a ninety degree rotation of locking element 850 about axis 882.

In one embodiment, implant 900 and complementary locking element 950 are as shown in FIGS. 9A-9D. For implant 900, unless otherwise noted, like reference numerals refer to like elements of implant 100, but within the 900 series of numbers. Additionally, it should be appreciated that ridges 932, 934 are reversed relative to the ridges of implant 100, but the ridge structures are otherwise the same as those described for implant 100 or contemplated alternatives.

Figure 9A:
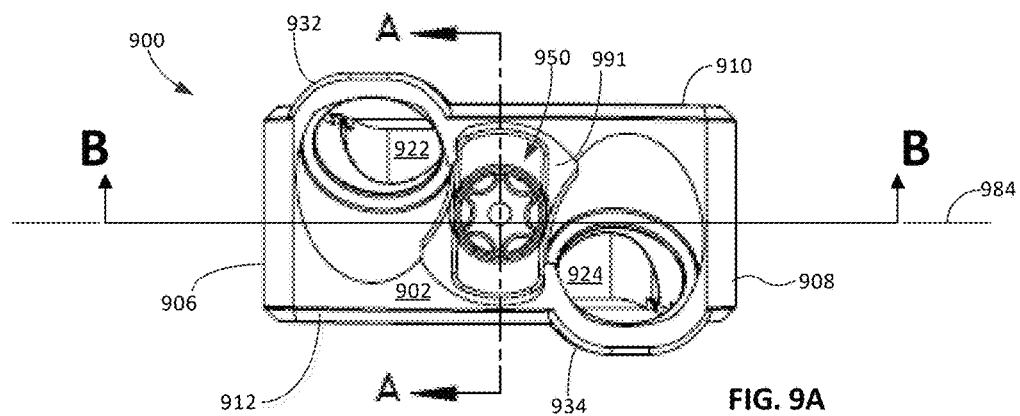
FIGS. 9A-9C are various views of an implant with a locking element disposed therein according to another embodiment of the disclosure.
Figure 9B:
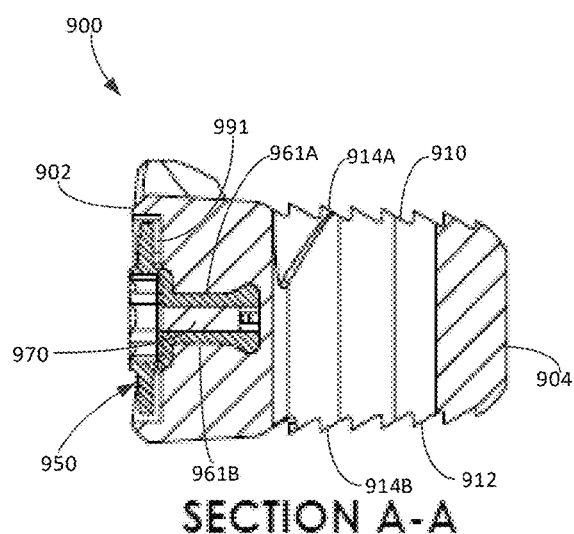
Figure 9C:
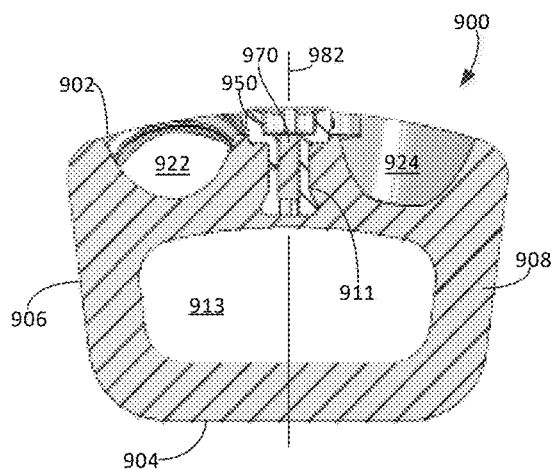

Implant 900 includes a recessed surface 991 internal to trailing surface 902, and recessed relative to recessed surface 991 is internal cavity 911, shown in FIGS. 9B and 9C. Internal cavity 911 is generally of uniform size, though widens at its terminal end remote from trailing surface 902. Recessed surface is sufficiently interior to trailing surface 902 so that locking element 950 head is disposable therein while internal cavity 911 is sized to receive a shaft in the form of flexible bars 961A, 961B extending from head 952 of locking element 950. As shown in FIGS. 9B and 9C, locking element 950 is hollow with a central passage of sufficient size to accommodate disposal of pin 970 therein.

Figure 9D:
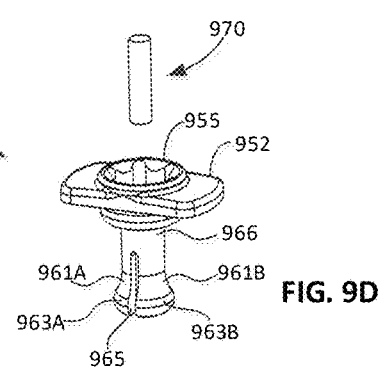
FIG. 9D is a perspective view of the locking element of FIG. 9A.

As shown in FIG. 9D, locking element 950 includes head 952 and a shaft 966 extending therefrom. Shaft 966 splits into two flexible bars 961A-B, separated by a slit 965. At free ends of each flexible bar are protrusions 963A, 963B extending outward from the shaft in opposite directions. Locking element 950 includes a drive element 955 and an opening or cannulation is internal to the drive element for disposal of a pin therein.

In an assembled condition, with locking element 950 disposed in implant 900 via a snap fit, pin 970 is placed within locking element 950 and protrusions 963A-B at a free end of the locking element are pushed outward against the walls of internal cavity 911, thereby holding locking element 950 in place within the implant. The inclusion of pin 970 within locking element 950 prevents withdrawal of the locking element from the implant. Both locking element 950 and pin 970 provide an interference fit engagement.

Figure 10:
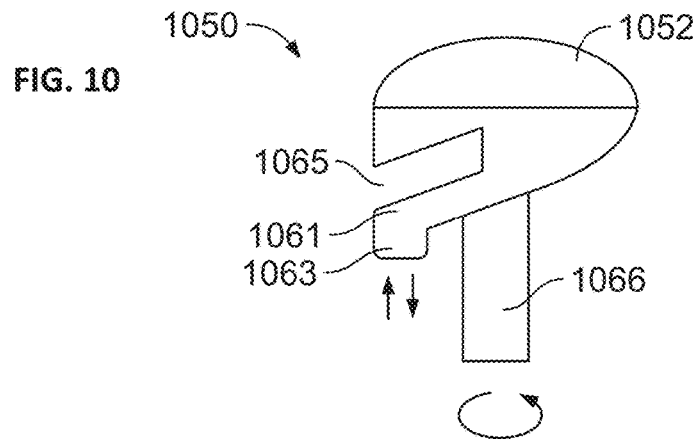
FIG. 10 is a side view of a locking element according to another embodiment of the disclosure.

The implant and locking element may, together or independently, be varied in many ways. For example, in one embodiment, a locking element may engage an implant with a snap fit in a longitudinal direction instead of a radial direction, as with locking element 1050 shown in FIG. 10. Locking element 1050 includes head 1052 and shaft 1066 extending therefrom. Within head 1052 is a flexible bar 1061 separated by the remainder of the head by slot 1065. At a free end of flexible bar 1061 is a protrusion 1063 extending toward a free end of shaft 1066. With locking element 1050, screws in an intervertebral implant may be blocked by snapping locking element 1050 into exterior/outward facing notches or recesses in the implant. The locking element is adapted so that when rotated, flexible bar 1061 bends inward and narrows slot 1065 to disengage from a notch, then once rotated to another notch, snaps back into place.

Figure 11:
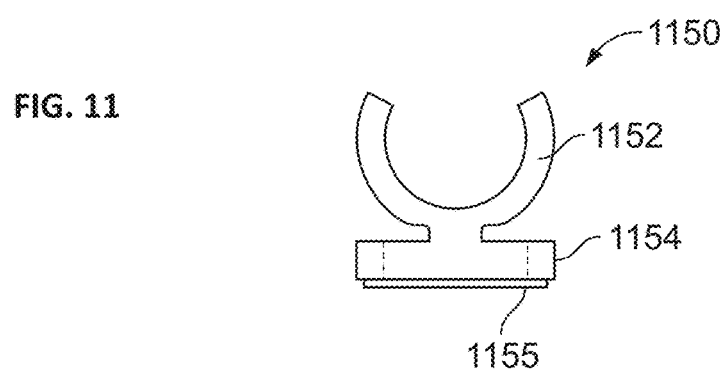
FIGS. 11, 12A-12B are various views of a locking element according to another embodiment of the disclosure.
Figure 12A:
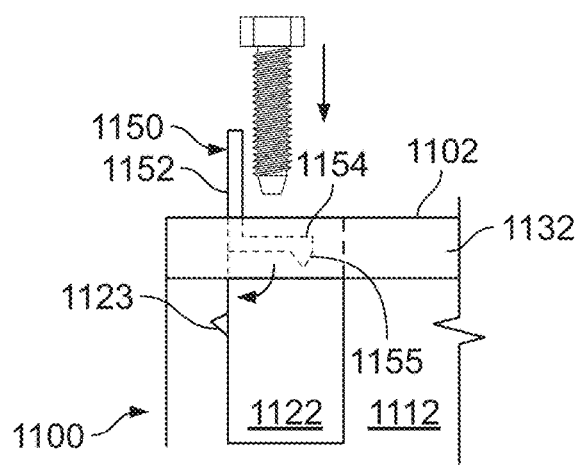
Figure 12B:
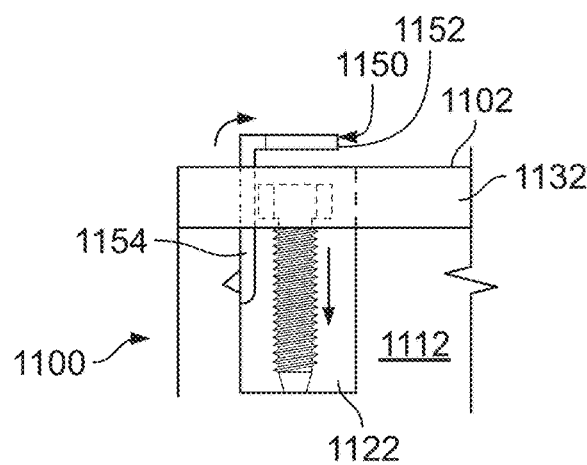

In another example, a locking element for an implant is in the form of a lever mechanism 1150 that is rotatable into a final position to hold a screw in place in the implant and prevent back out. For example, in FIGS. 11 and 12A-B, lever mechanism is a two-part structure pivotable about a meeting point between the two parts. A first part 1152 and a second part 1154 of the lever mechanism are both U-shaped. The U-shaped bodies of lever mechanism 1150 are sized to be narrower than a head of a screw to be inserted into the implant. Second part 1154 is orthogonal to first part 1152. At a free end of second part 1154 remote from the first part is an engagement feature 1155. In some variations, a diameter of second part 1154 is less than a diameter of first part 1152. Lever mechanism 1150 is fixed to an implant 1100 at a juncture between the two parts, as shown in FIGS. 12A, 12B and is positioned so that it is rotatable until second part 1154 engages a wall of opening 1122 and engagement feature 1155 locks into place within a second engagement feature 1123.

In still further examples, two or more of the locking element structures and concepts described herein may be included on a trailing surface of an intervertebral implant to block, collectively, three or four or more bone fasteners. In other examples, a locking element may be used to block a single bone fastener.

Figure 25A:
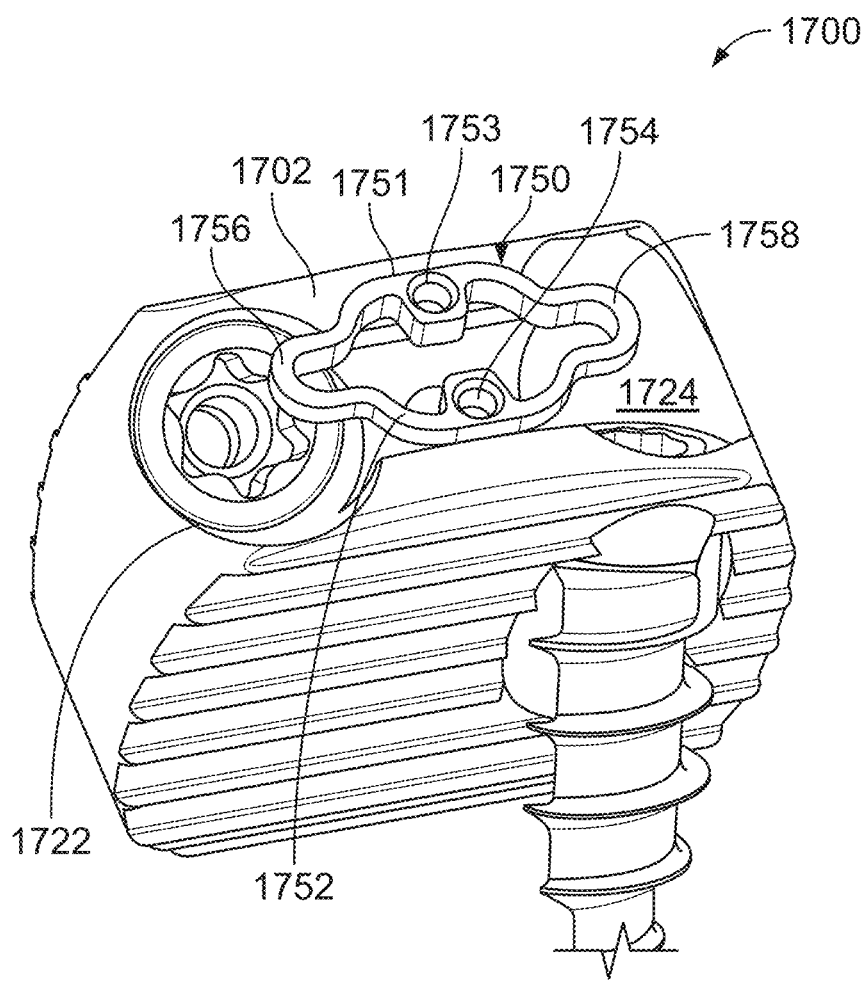
FIGS. 25A-B are perspective and close up sectional views of a first step in a method of assembly of an intervertebral implant according to one embodiment of the disclosure.

In another embodiment, an implant 1700 includes a locking element 1750 in the form of a wave spring, as shown in FIGS. 25A-26B. For implant 1700, unless otherwise noted, like reference numerals refer to like elements of implant 100, but within the 1700 series of numbers. Implant 1700 is sized to receive locking element 1750 and includes a recessed surface 1791 on its trailing surface 1702, as shown in FIG. 25B, for example. Recessed surface 1791 extends between openings 1722, 1724, the openings being for receipt of fasteners within the implant. Along superior and inferior sides of recessed surface 1791 are grooves 1788, 1789 shown in FIG. 25B. Locking element 1750 is flexible and sized to snap into grooves 1788, 1789, as described in greater detail in the method. Locking element 1750 includes a widened central region with side portions 1751, 1752, and narrowed, loop ends 1756, 1758. Collectively, side portions and narrowed loop ends from a continuous, enclosed structure, as shown in FIG. 25A. Locking element 1750 has a length such that, when overlaid or within trailing surface 1702, each loop end 1756, 1758 covers a respective opening 1722, 1724 in the implant. Further, when the locking element is not compressed, a dimension between outside edges of side surfaces 1751, 1752 is greater than a width into recessed surface 1791. On respective side portions 1751, 1752 are inward facing enclosed structures that encircle holes 1753, 1754. Holes 1753, 1754 are sized for engagement with a holding instrument.

Figure 13:
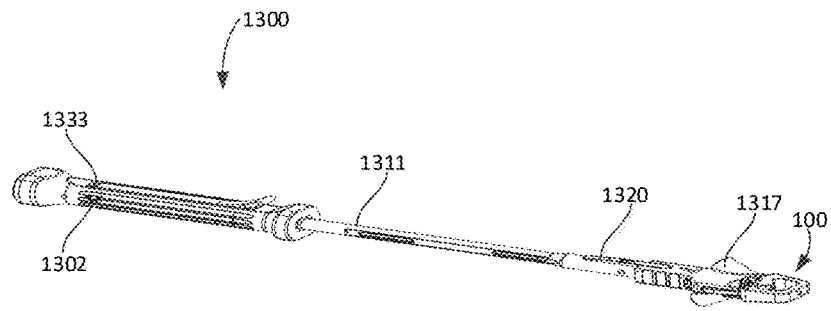
FIGS. 13, 14A, 14B are views of an implant inserter system and implant according to another embodiment of the disclosure.
Figure 17:
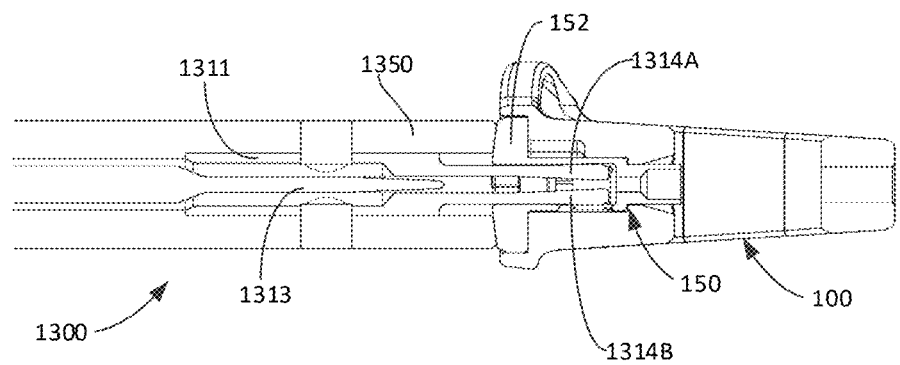
FIGS. 17-18 are steps in a method of engaging an implant with the inserter of FIG. 13 according to another embodiment of the disclosure.
Figure 18:
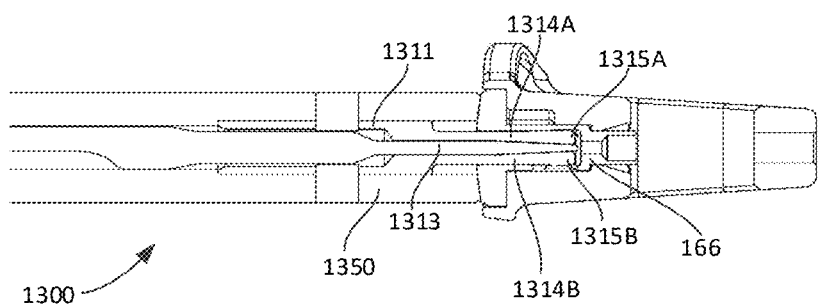

In another aspect, the present disclosure relates to an insertion instrument. In one embodiment, insertion instrument 1300 is as shown in FIGS. 13, 14A, 14B and 17-18. With reference to FIG. 13, insertion instrument 1300 includes a handle 1302 and an outer shaft 1311 extending from the handle. Additionally, within the handle and outer shaft is an axially translatable inner shaft 1313 shown in FIGS. 17-18. At a distal end of insertion instrument 1300, opposite handle 1302, are engagement features for engagement to an implant, such as implant 100 shown engaged to the insertion instrument in FIGS. 13, 14A, 14B and 17-18. Outer shaft 1311 is generally tubular and extends to a distal end. From the distal end of outer shaft are first and second longitudinally extending prongs 1314A, 1314B, both of which extend to free ends, as shown in FIGS. 17 and 18. Toward the free ends of first and second prongs 1314A, 1314B, each prong becomes wider in a direction facing the opposite prong. These widened tips are denoted by reference numerals 1315A, 1315B, respectively. Through this structure, each prong 1314A, 1314B at the distal end of the instrument enlarges upon advancement of inner shaft 1313 into the distal region of the instrument, thereby promoting engagement between the instrument and the subject of its engagement, such as an intervertebral implant. In an alternative configuration, the tubular outer shaft may extend to the distal end and include circumferentially spaced slots so that the entire tubular structure of the outer shaft expands upon receipt of the inner shaft as it advances distally. In further variations, the reverse-taper of the prongs may be substituted with protrusions having other shapes that provide an increased thickness at the distal end of the insertion instrument.

Figure 14A:
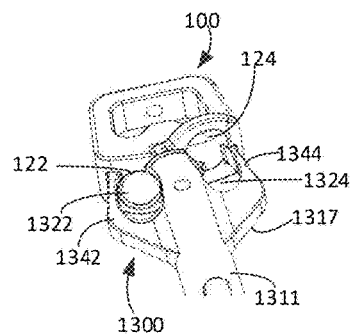

With continued reference to a distal region 1317 of insertion instrument 1300, distal region includes a widened body with angled fastener openings 1322, 1324 passing therethrough, as best shown in FIG. 14A. The fastener openings are positioned and angled to correspond to openings in the implant to be implanted, e.g., openings 122, 124 for implant 100. This arrangement is advantageous in that bone fasteners may be inserted into an implant while the insertion instrument is engaged to the implant, with space available to do so as shown in FIG. 14A. Peripherally and extending longitudinally on the outsides of fastener openings are alignment arms 1342, 1344, each including an inward facing prong (not shown) at a respective free end. While engaged to an implant, such as implant 100, the prongs of arms 1342, 1344 engage within notches 138A, 138B of the implant. The arms are advantageous in that while engaged to notches in the implant, the rotation of the implant relative to the insertion instrument is minimized.

Axial translation of inner shaft 1313 is controllable through a position of lever arm 1334 relative to handle 1302. In particular, rotation of lever arm 1334 about a pivot point at base 1333 causes inner shaft 1313 to move axially. Because the pivot point for lever arm is offset relative to a connection point between the lever arm and inner shaft 1313, rotation of the lever arm causes inner shaft to be pushed or pulled with respect to the base of the lever arm upon its rotation.

In one specific example of the actuation mechanism for the insertion tool, the actuation mechanism and the lever arm are connected to one another through an internal link. The internal link is connected to the inner shaft at one end and the lever arm at the other end, with a pin connection at both ends. The lever arm 34 is connected to the handle via a third pin separate from the first and second pins, and located at a location closer to an internal end of the lever arm than the pin for the internal link. Through the pin connection, the lever arm is pivotable about an axis through the third pin. In certain additional examples, a bottom surface of the handle opposite the lever arm includes a lock button that is secured to the handle via a pin that is threaded into a corresponding thread in a ball detent, disposed internally within the handle. The ball detent is disposed within the handle such that it lies immediately proximal to an internally disposed portion of lever arm. Proximal to the ball detent is a spring and then an end cap closing the enclosed channel of the handle at an end of insertion instrument. Through this assembly, the ball detent is axially adjustable from a biased position abutting the lever arm to a retracted position, with spring compressed, that is spaced apart from the lever arm. Through operative connection of the ball detent with the lock button, lock button is actuatable to retract the ball detent. This specific configuration provides a mechanism to control whether the lever arm may be rotated. When the lock button is retracted, the lever arm may be rotated. When the lock button is not, then the lever arm is locked in place. Thus, the operative connection between the lever arm and the inner shaft is such that rotation of lever arm 1334 about the base causes inner shaft 1313 to move axially either distally or proximally.

Figure 14B:
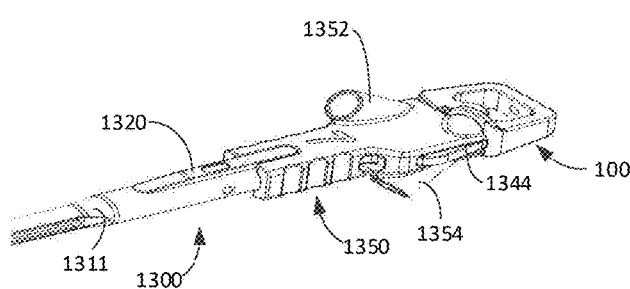

Toward a distal end of outer shaft 1311 is a button 1320 secured thereto via internal springs (not shown) internal within the outer shaft. Without load applied to button 1320, button 1320 is biased in a raised position relative to a surface of outer shaft 1311, as shown in FIG. 13, for example. However, button 1320 may be depressed with the application of forces thereon, thereby compressing the internal springs. One function of the button is to prevent axial movement of drill guide 1350 in a proximal direction when attached to insertion instrument 1300, as shown in FIG. 14B. In some examples, outer shaft 1311, towards its distal end, also includes a pair of engagement features on opposing lateral sides that are in the form of longitudinally extending slots. These slots are sized for the disposal of engagement features of a drill guide 1350 therein.

Figure 19:
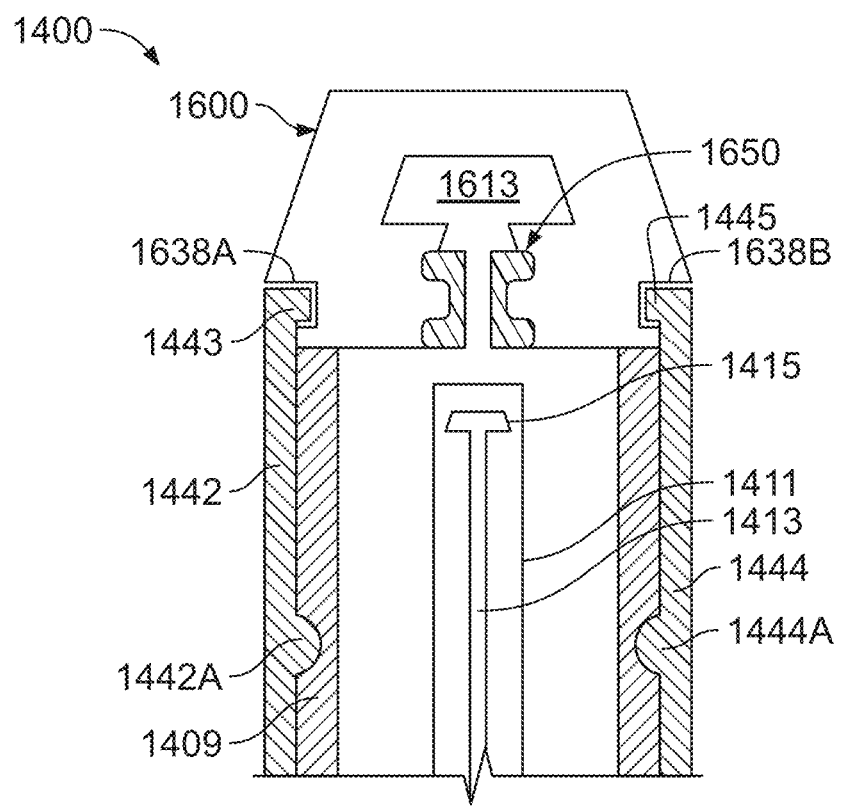
FIGS. 19-20 are steps in a method of engaging an implant with an inserter according to another embodiment of the disclosure.
Figure 20:
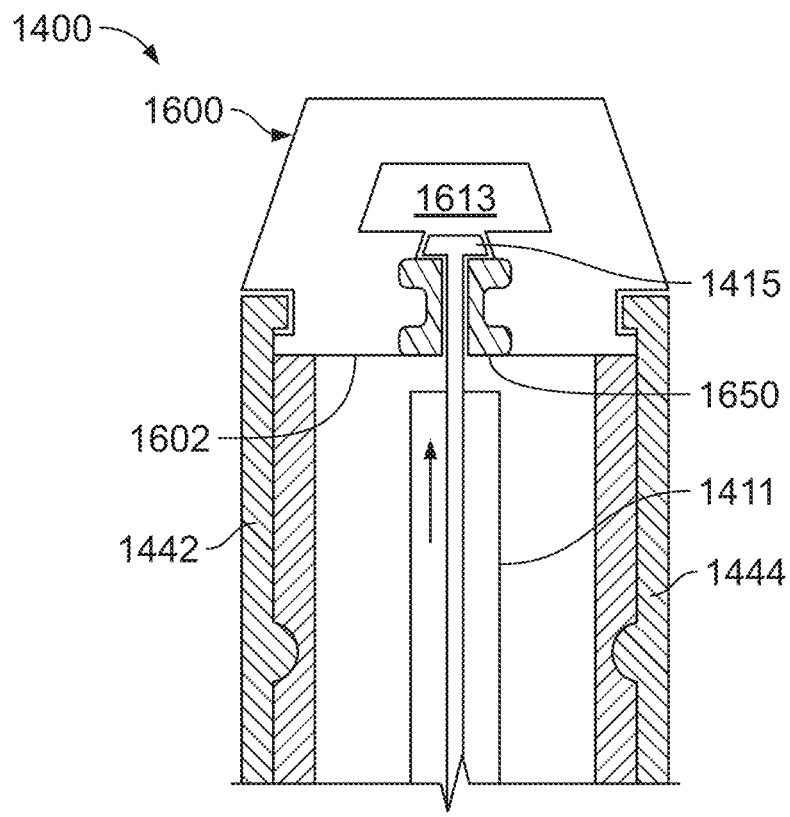

In another embodiment, insertion instrument 1400 is shown in FIGS. 19-20. Insertion instrument 1400 includes a cannulated outer shaft 1409 with distally extending end arms 1442, 1444 that extend longitudinally from an end region of the outer shaft. Each end arm 1442, 1444 is pivotably connected to the outer shaft so that inward facing protrusions 1443, 1445 at the ends of the respective arms 1442, 1444 may be actuated through pivoting of arms 1442, 1444. A sleeve slidable over arms 1442, 1444 may be included to function as an actuation mechanism, the sleeve sliding along a length of the arms to control their orientation relative to a central axis of the instrument. In an alternative arrangement, arms maybe flexibly connected to the outer shaft and bend in an outward direction upon application of force from an inside of the arms. In such an arrangement, the arms may be biased to be parallel with the central axis of the instrument or biased slightly inward. Arms 1442, 1444 may extend from outer shaft 1409 at respective hinge points, e.g., 1442A, 1444A, respectively. It should be appreciated that the actuation function of arms 1442, 1444 may be derived from a variety of arrangements. For example, from active control, the material properties of the arms themselves or from a living hinge, among others. Internal to outer shaft is cannulated intermediate shaft 1411, and internal to intermediate shaft 1411 is inner shaft 1413 with a head 1415 extending radially outward relative to a central longitudinal axis of inner shaft 1413. In some examples, head is closer in size to inner shaft 1413. In those and other examples, head may be threaded. In other alternatives, any number of inner or outer sleeves and or shafts may be included with the instrument.

As shown in FIGS. 19-20, protrusions 1443, 1445 on arms 1442, 1444 are sized for engagement within notches, e.g., 1638A, 1638B on implant 1600, on corner surfaces at the sides of an intervertebral implant while head 1415 of inner shaft 1413 is disposable within a complementary cavity within an appropriately sized implant, e.g., implant 1600. Further, head 1415 may have elastically deformable physical properties to provide for bending of head 1415 when pressed against surfaces so that head 1415 may be advanced through passages smaller than dimensions of the head, such as a cannulation through a locking element, e.g., locking element 1650. In some examples, implant 1600 may include threads on an interior surface adjacent to locking element 1650, the threads being complementary to threads on head 1415 of inner shaft 1413. In some examples, inner shaft 1413 may have both a smaller size than head 1415 and less flexibility while still being translatable through locking element 1650 in implant 1600.

Figure 15:
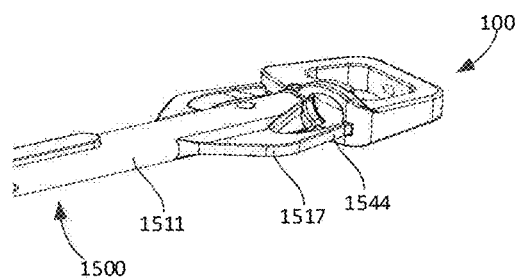
FIGS. 15 and 16 are views of an implant inserter system and implant according to another embodiment of the disclosure.
Figure 16:
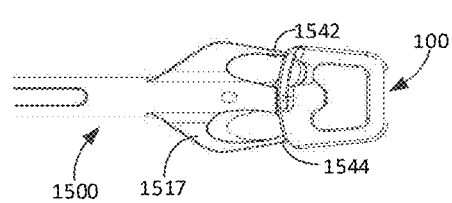

In another embodiment, an insertion instrument appears as shown in FIGS. 15 and 16. Unless otherwise noted, like reference numerals refer to like elements of the insertion instrument 1300, but within the 1500 series of numbers. Insertion instrument 1500 is adapted for use with a variety of implant sizes although does not include openings to provide for fastener insertion while engaged to an implant.

The insertion instrument may be varied in many ways. For example, the distal end region of the outer shaft and/or intermediate shaft may include prongs adapted to engage interior walls of an implant where the implant does not include a locking element disposed therein. This design may be desirable where a locking element to be used is not cannulated.

In yet another aspect, the present disclosure relates to a system including an insertion instrument and an intervertebral implant. In some embodiments, an insertion instrument such as those described herein may be used in conjunction with any implant having a vacant central opening so that longitudinally extending prongs of the insertion instrument may be inserted therein. For instance, with embodiments of the implant having an opening through the locking element. In other embodiments, a system includes an insertion instrument, an intervertebral implant and a drill guide structure, such as drill guide 1350 shown in FIG. 14B. Drill guide 1350 includes a longitudinally extending engagement feature (not shown) along its length to engage with an insertion instrument and may be held in place axially through a back stop provided by button 1320, again, as shown in FIG. 14B. Drill guide 1350 includes guide holes 1352, 1354 protruding from a main body and angled in opposite directions, the angulation corresponding to an angulation of openings in the implant attached to the insertion instrument.

In yet another aspect, the present invention relates to a method of manufacturing an intervertebral implant. In some embodiments, the implant is formed using an ALM fabrication process such as SLS, SLM or EBM described above, fused deposition modeling (FDM), or another appropriate 3D printing technology known to those skilled in the art.

When employing powder-bed based technologies, articles are produced in layer-wise fashion according to a predetermined digital model of such articles by heating, e.g., using a laser or an electron beam, multiple layers of powder, which may be a metallic powder, that are dispensed one layer at a time. The powder is sintered in the case of SLS technology and melted in the case of SLM technology, by the application of laser energy that is directed in raster-scan fashion to portions of the powder layer corresponding to a cross section of the article. After the sintering or melting of the powder on one particular layer, an additional layer of powder is dispensed, and the process repeated, with sintering or melting taking place between the current layer and the previously laid layers until the article is complete. The powder layers similarly may be heated with EBM technology. Additive manufacturing techniques such as the ALM processes described above may be employed to form the implant, the locking element, or the combination of the implant and the locking element. It should also be appreciated that other devices, instruments, or components therefor that are contemplated by this disclosure may also be formed through an ALM process. In some instances, materials for one layer may be different than the materials for successive layers.

In some embodiments, an implant and accompanying locking element are formed through a single, continuous ALM process. Put another way, the combined structures are formed layer by layer through a single step. This approach may be employed to form any one of implants 100, 200, 300, 400, 800, 900, for example. The geometry and other properties of the implant and the locking element are programmed into software associated with the ALM system, e.g., computer and machine, and then used to produce both elements together in a single pass. When complete, the locking element is located either on the implant (e.g., implants 100, 800, 900) or in the implant (e.g., implants 200, 300, 400).

In some embodiments, an implant is formed through a two-step ALM process where a first part of the implant is formed via ALM, then paused, and then later resumed to completion. This ALM process is focused on the implant itself and does not include formation of the locking element, as described in greater detail below. The two-step approach is particularly well suited for implants with a locking element enclosed within the implant. More particularly, where the locking element is not formed through ALM, this approach facilitates the inclusion of such locking elements in the implant even when the locking element is disposed in an internal cavity of the implant without openings large enough to insert or remove the locking element. The two-step process has particular applicability as an option for implants 200, 300, 400, 500, 600, 700, 800 for example.

Turning to the details of the process, a first portion of an implant is formed through an ALM technique. With reference to implant 200 as illustrative, printing begins from leading surface 204 and continues toward an opposite end of the implant until just shy of trailing wall 203. These locations on implant 200 are best shown in FIGS. 2A and 2B. To perform the first step, a mold may be used to keep the partially formed implant in a fixed location. Upon reaching a location of the implant structure approximately where head 252 of locking element 250 would be disposed, printing is stopped. Then, locking element 250 is retrieved and disposed in a formed portion of cavity 211 of implant 200. Locking element 250 may be formed by any desired method, either subtractive or additive. Of course, as noted above, locking element 250 may also be formed together with the implant body in a single continuous process. Locking element 250 is checked to confirm it is positioned within cavity 211 at a sufficient depth, then step two of the process may commence. ALM resumes and the remainder of the implant is printed, including trailing wall 203. In each of the first and second steps, the same pre-programmed model is used to print the implant, so the final implant, even with the break in printing, still reflects the desired properties and dimensions. Indeed, the final implant is a monolithic structure. This method may be similarly performed for implants 300, 400, 500, 600, 700. For implant 800, a first step involves printing implant 800 from surface 804 to a location on the implant aligned with the narrower portion of the locking element. Then, printing is paused and locking element 850 is inserted from opening 813 into its intended position within the implant. To continue, locking element may need to be temporarily held in place so that it does not become displaced. The second step is then performed by printing the remainder of implant 800 up to surface 802 so that locking element 850 is entirely held within implant 800, as shown in FIG. 8B.

In yet another embodiment, the implant itself may be formed in its entirety through ALM in a continuous single step process without the locking element. In this method, the locking element may be inserted into the implant after formation of the implant via ALM. In some cases, an implant may simply be inserted into a cavity on a trailing surface of the implant, such as with implants 100, 900. In other examples, the cavity for the implant is blocked from the trailing side. In these examples, the implant includes access passages, i.e., slots, so that the locking element may be slid into the cavity within the implant and secured in place with a pin, for example. Examples of the latter configuration include implants 500, 600, 700. With reference to implant 500 as illustrative, implant 500 is first formed through a single step continuous ALM process, layer by layer. Then, locking element 550 is slid into cavity 511 through either side access 526 or side access 527, as shown in FIG. 5D. Insertion may involve first orienting locking element 550 so its long dimension is perpendicular to a length of the side access opening edge and then advancing it into one of openings 522, 524 before pushing it into one of the side access openings. Once locking element 550 is centered on central longitudinal axis 582, pin 570 is used to secure locking element 550 in place. In this method, locking element 550 may be formed through ALM or any other manufacturing process.

Materials used to form the implant, locking element and/or various components described above with an ALM process include, but are not limited to, metals (e.g., metal powder) that may be any one or any combination of titanium and its alloys, stainless steel, magnesium and its alloys, cobalt and its alloys including cobalt chromium alloys, nickel and its alloys, platinum, silver, tantalum niobium, and other super elastic materials such as copper-aluminum alloys. Of the aforementioned examples, titanium is particularly well suited for the implants described herein. Non-metallic materials may also be used and include, but are not limited to, implantable plastics. These may be any one of or a combination of wax, polyethylene (PE) and variations thereof, polyetheretherketone (PEEK), polyetherketone (PEK), acrylonitrile butadiene styrene (ABS), silicone, and cross-linked polymers, bioabsorbable glass, ceramics, and biological active materials such as collagen/cell matrices. Of the aforementioned examples, PEEK is particularly well suited for the implants described herein. Combinations of material types are also contemplated. For example, the implant may be formed of a titanium coated PEEK. To the extent other materials are described elsewhere in the specification, such materials are also contemplated for use in ALM processes.

Figure 21:
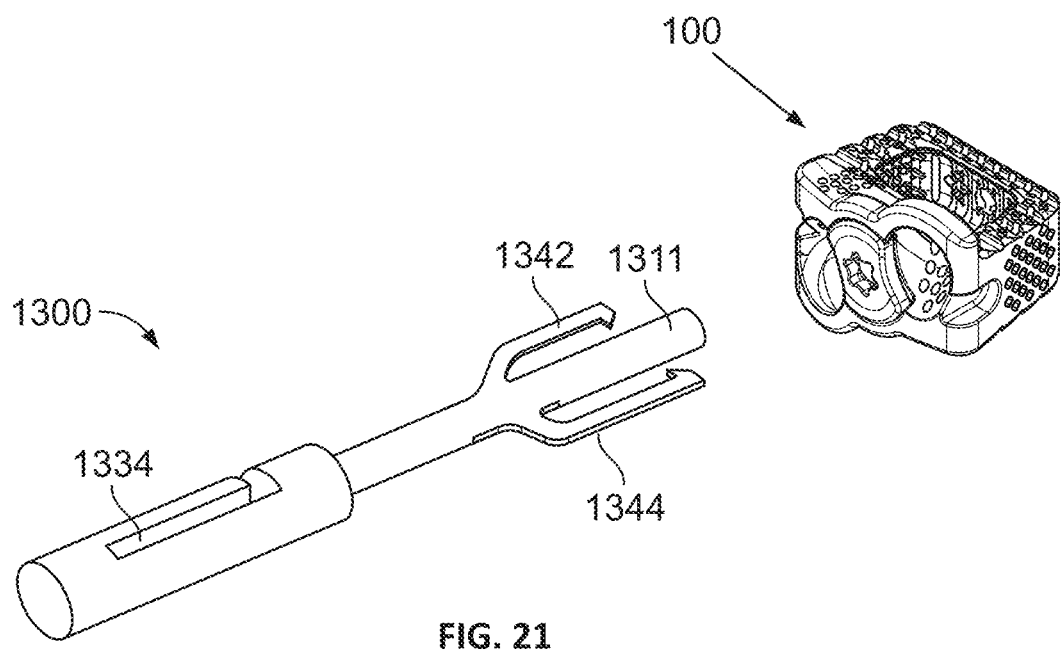
FIGS. 21-24 are steps in a method of implanting an intervertebral implant into an intervertebral space according to another embodiment of the disclosure.

In yet another aspect, the present disclosure relates to a method of implanting an intervertebral implant using an implant insertion instrument. In some embodiments, insertion instrument 1300 is used to perform the method. For purposes of illustration, the method will be described with reference to implant 100, the details of which are shown in FIGS. 1A-1G, for placement into an intervertebral space. Initially, insertion instrument 1300 is engaged with implant 100, as shown generally in FIG. 21. Because locking element 150 is built into central longitudinal opening 111 of implant during manufacture, i.e., prior to surgery, as shown in FIG. 1B, no additional step is required during surgery to engage implant 100 with insertion instrument.

To engage the insertion instrument with implant 100, arms 1342, 1342 are advanced into engagement with notches 138A, 138B on sides of trailing surface 102. Engagement of the arms to the sides of implant stabilizes the implant relative to the insertion instrument and prevents relative rotation. At the same time, a distal end of outer shaft 1311 is advanced into a cavity 153 within locking element 150 disposed in implant 100, a step illustrated in FIG. 17. Then, lever arm 1334 is rotated toward the user to push inner shaft 1313 within outer shaft 1311, advancing inner shaft 1313 as represented in a comparison of FIGS. 17 and 18. As inner shaft 1313 passes between longitudinally extending prongs 1314A, 1314B at a distal end of the outer shaft, exterior surfaces of the prongs press against the inner walls of shaft 166 of the locking element. In turn, pressure is applied from shaft 166 onto walls of central longitudinal opening 111. Thus, in the engaged position, pressure from prongs 1314A, 1314B against locking element 150 holds implant 100 in place relative to insertion instrument 1300, while arms 1342, 1344 prevent relative rotation between the implant and the insertion instrument.

Figure 22:
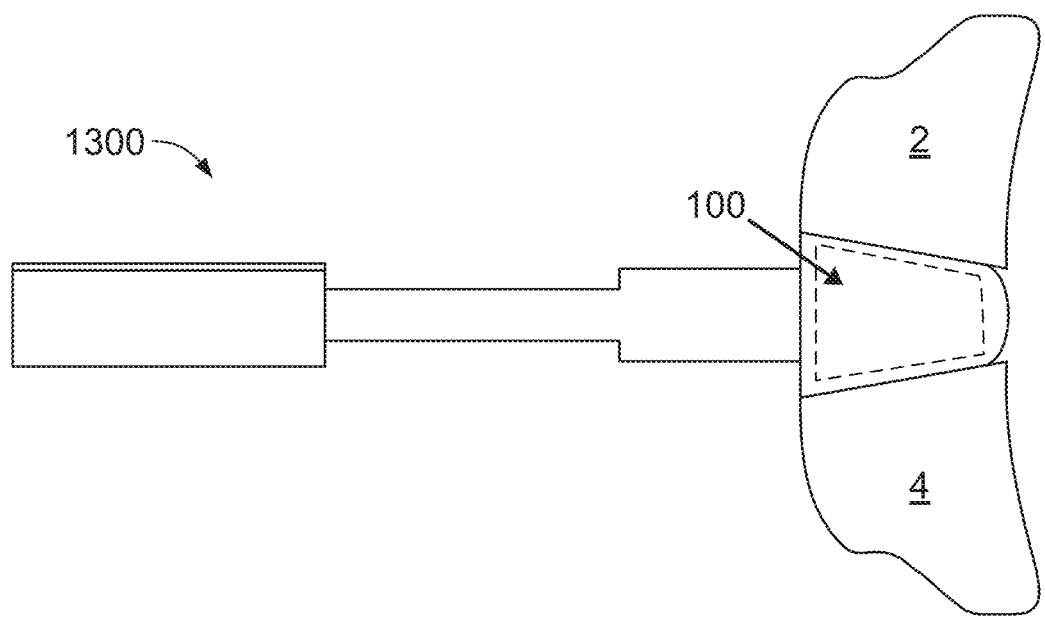
Figure 23:
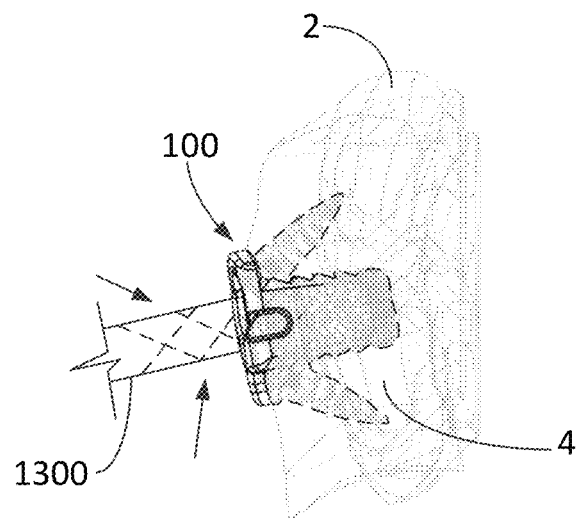

At this juncture, the insertion tool is used to advance the implant into a prepared intervertebral space between vertebrae 2, 4, as shown in FIG. 22. Then, fasteners are inserted into respective openings 122, 124 in implant 100, as shown in FIG. 23. Optionally, a drill guide, such as drill guide 1350, may be slid onto insertion instrument 1300 into a position shown, for example, in FIG. 14B, prior to the fastener insertion step to provide additional guidance for the fastener insertion. In either variation, the fasteners may be advanced into respective vertebrae adjacent to the implant with the insertion instrument engaged to the implant, as shown in FIG. 23. This is made possible by the angled open pathways 1322, 1324 built into distal region 1317 of insertion instrument 1300, and, by extension, the guide paths 1352, 1354 built into drill guide 1350, as applicable. Due to the trajectory of openings 122, 124 in implant 100, each fastener may be anchored at a steep angle to provide for anchorage into an outer corner of a respective vertebra when inserted therein.

Figure 24:
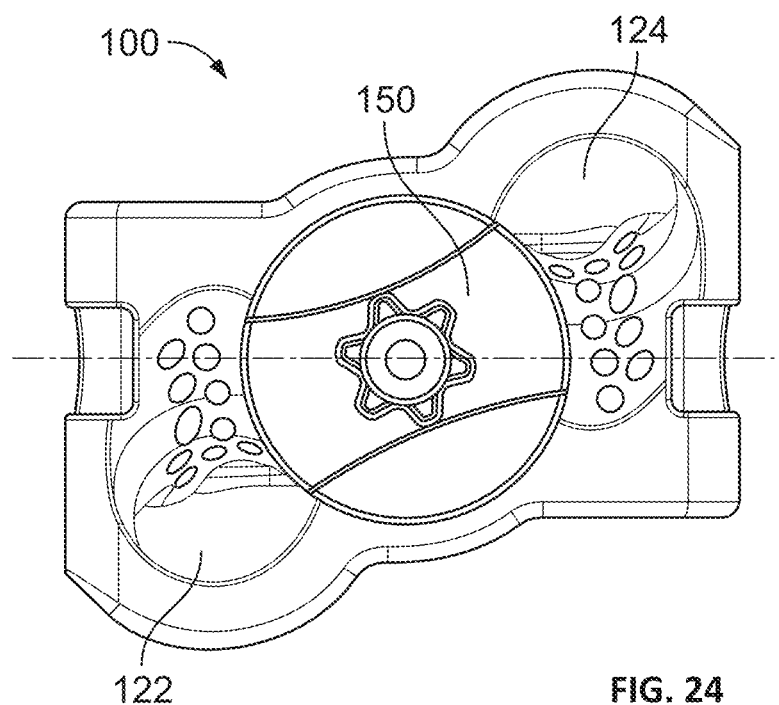

Once the user is satisfied with the implant position in the intervertebral space and the fastener anchorage, instrument 1300 is removed and locking element 150 is rotated into a blocking position, as shown in FIG. 24, to prevent back out of fasteners (fasteners not shown in FIG. 24). With respect to implant 100 specifically, a driver is used to engage drive element 155, and locking element 150 is rotated ninety degrees to shift the end portions of locking element 150 from a superior-inferior orientation outside of the path of openings 122, 124 to a sideways oriented direction whereby each end portion blocks a respective opening 122, 124. The locking element provides a visual of the partial coverage of the fastener heads in openings 122, 124. Also, the locking element provides a tactile and audio feedback as it is rotated into a new locked position. For example, as the locking element is rotated into the blocking position, it makes a snap sound as it locks into place, and the user can also feel, through the driver engaged to the locking element, that the locking element is moved into a new locked position. Some or all of these visual, audio and tactile feedback mechanisms are similarly present in other implants described in the present disclosure. This completes the implantation of implant 100. The method may be similarly performed with implant 300.

The method of implantation may be varied in many ways. With continued reference to insertion instrument 1300, in some examples, a locking element is inserted into the implant and secured with a pin during manufacture prior to use of the implant in surgery. For instance, with implants 500, 600, 700, the locking element may be slid into the implant from a side access, e.g., 526, 527 shown in FIG. 5D, that is accessible from a fastener opening in the implant. With implants 600, 700, the locking element may be inserted through an inferior access in the implant, e.g., 629, 729, shown in FIGS. 6D and 7D. Then, a pin may be inserted through the central opening in the locking element to secure the locking element in place. For implant 900, locking element 950 and pin 970 may be snapped into place during manufacture of the implant. In other examples, such as with implants 200, 300, 400, 800, the implant may be formed with the locking element together in an additive manufacturing process so there is no separate locking element insertion step.

Figure 25B:
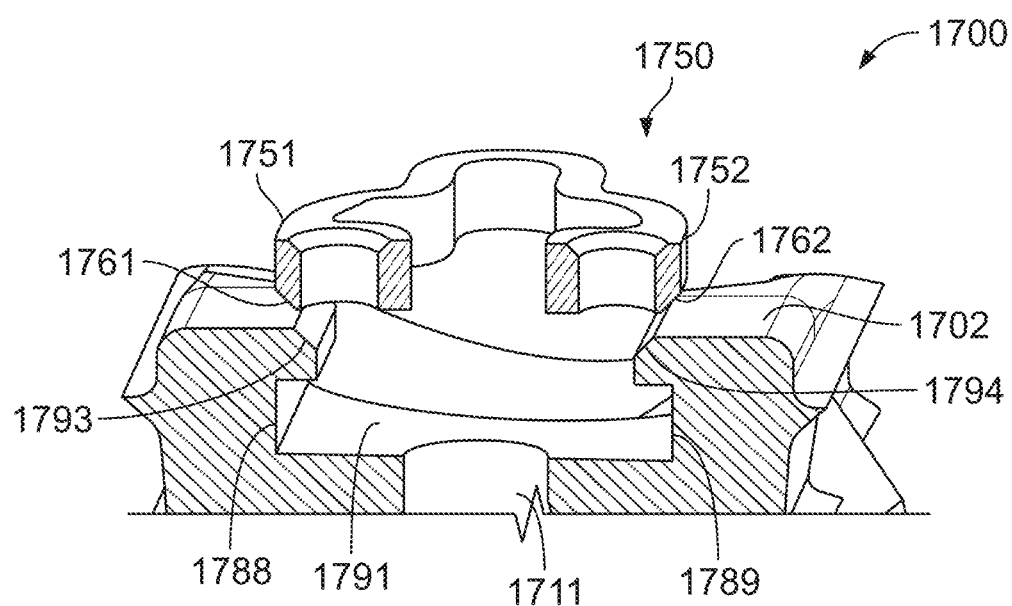
Figure 26A:
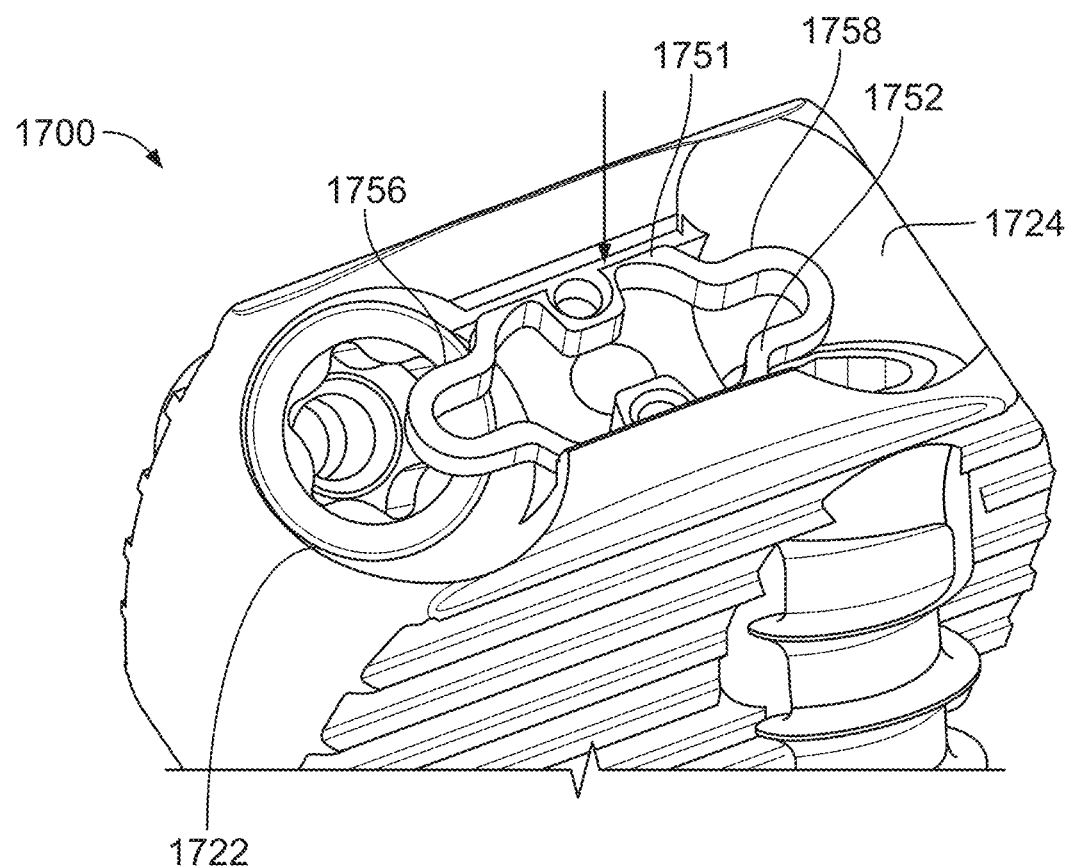
FIGS. 26A-B are perspective and close up sectional views of a second step in the method of assembly of the intervertebral implant of FIGS. 25A-B.
Figure 26B:
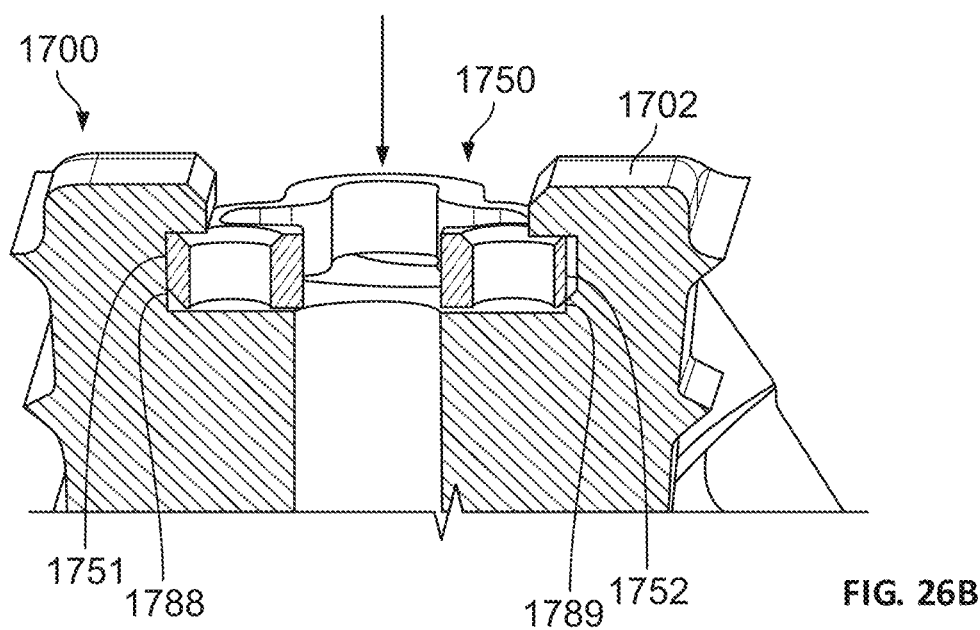

In another example, locking element 1750 is inserted into implant 1700. Initially, locking element 1750 is advanced toward trailing end 1702 of implant, as shown in FIGS. 25A-B. An instrument may be used to direct the locking element to the implant through insertion of arms on the instrument through openings 1753, 1754. Alternatively, the locking element may be engaged with another instrument or may be held by hand and placed into the implant. As locking element 1750 contacts trailing surface 1702, chamfers 1761, 1762 on locking element 1750 contact implant chamfers 1793, 1794. As these surfaces contact one another and the locking element is advanced toward recessed surface 1791, side portions 1751, 1752 flex inward to slide over the lip around the recessed surface of the implant, and then locking element 1750 snaps into place within recessed surface 1791. In particular, side portions 1751, 1752 snap into grooves 1788, 1789, as shown in FIGS. 26A-B. When engaged in grooves 1788, 1789, side portions 1751, 1752 are in tension, thereby holding locking element 1750 in place within implant 1700. In this position, loop portions 1756, 1758 are positioned to block openings 1722, 1724. During use of the implant during surgery, screws may be inserted through openings 1722, 1724 prior to engagement of locking element 1750 to implant 1700.

In yet another variation of the method, applicable to implants 200, 400, 500, 600, 700, 800, 900, the locking element may be modified to include a central longitudinal cavity for gripping by insertion instrument 1300 to insert the instrument into the implant. For implants that include a pin to secure the locking element, the pin may be enlarged and include a cavity therein for insertion of prongs 1314A, 1314B. In other examples, when an implant from among implants 200, 400, 500, 600, 700, 800, 900 is used but is not modified for insertion of the prongs of instrument 1300, another instrument may be used to hold the implant and place it into the intervertebral disc space. For instance, an alternative instrument may be forceps or another insertion device with gripping arms structured for engagement with the fastener openings in the implant. Thus, if forceps are used to engage with implant 200 and deliver it to a target space in the spine, then the forceps may grip fastener openings 222, 224 to hold the implant. In this manner, a fully assembled implant, here, implant 200 with locking element 250 disposed therein, may be delivered to a target site in a patient even without a custom opening in the locking element for engagement by insertion instrument 1300. Once implant 200 is in a desired position within the spine, the forceps may be removed and the fasteners implanted through the fastener openings. It should be appreciated that this method may also be used even when use of instrument 1300 is another available option, such as with implant 100.

In another embodiment, an implant may be implanted using insertion instrument 1400 in the same manner as that described for insertion instrument 1300. However, with insertion instrument 1400, widened head 1415 on inner shaft 1413 is advanced through a central opening in a locking element, e.g. locking element 1650 within implant 1600, and into a widened opening internal to the locking element, as shown FIG. 20. In some examples, a threaded connection is formed between head 1415 and implant 1600. In this position, inner shaft 1413 is held in place with respect to the implant. To pass through the opening in locking element, inner shaft may bend in an elastic manner. In some examples, the head may be sized to fit through an opening in locking element 1650. In some examples, arms 1442, 1444 may be actuated to lock into notches 1638A-B through advancement of a sleeve along the arms. In yet another embodiment, an implant may be implanted using insertion instrument 1500. Once implant is in position within an intervertebral space, instrument 1500 may be removed prior to advancing bone fasteners through the implant and into vertebral bone structures.

In some embodiments, the step of blocking fasteners inserted into an implant may be performed with locking mechanism 1150 instead of a locking element such as locking element 150, as shown in FIGS. 12A-B. With implant in place within an intervertebral disc space, a fastener is directed to an opening 1122 in implant 1100. As the fastener reaches second part 1154 of locking mechanism 1150, the head of the fastener having a diameter larger than that of second part 1154 causes the second part to be pushed and rotated downward with advancement of the fastener until second part 1154 contacts a wall of opening 1122, as shown in FIG. 12B. Engagement feature 1155 engages with second engagement feature 1123 to secure locking mechanism 1150 in position, and the fastener is prevented from back out by first part 1152, now parallel to trailing surface 1102 of implant 100.

It should be noted that any of the devices and methods disclosed herein can be used in conjunction with robotic technology. For example, any of the implants described herein can be used with robotic surgical systems to place the implant in a patient. The implant can be manipulated with a robotic system or a robotic arm to rotate or position the implant, and to anchor bone fasteners through the implant during a procedure. Further, any or all of the steps described in the methods for performing an implant placement procedure of the present disclosure may be performed using a robotic system. Similarly, robotics may be used in methods of forming the implant with ALM processes.

Although the disclosure herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of forming an intervertebral implant using additive layer manufacturing comprising:
alternately depositing and heating successive layers of a first source material to form a first portion of a body of the intervertebral implant;
alternately depositing and heating successive layers of a second source material subsequent to the formation of the first portion to form a fastener blocker; and
alternately depositing and heating successive layers of the first source material subsequent to the formation of the first portion to form a second portion of the body,
wherein the depositing and heating steps result in the fastener blocker being captured between the first and second portions such that a head of the fastener blocker is contained within the body, and
wherein the fastener blocker is configured to be moveable between a first position where the fastener blocker blocks at least part of an opening in the body and a second position where the fastener blocker does not block any part of the opening.

2. The method of claim 1, wherein upon formation of the second portion, the fastener blocker is irremovably enclosed within the body.

3. The method of claim 1, wherein the additive manufacturing process is continuous such that the body and the fastener blocker are formed together in a single sequence.

4. The method of claim 1, wherein the first source material is different from the second source material.

5. The method of claim 1, wherein at least a portion of the body is formed simultaneously with at least a portion of the fastener blocker.

6. The method of claim 1, further comprising:
forming one or more struts on the first portion of the body; and
forming the fastener blocker such that the fastener blocker is attached to the one or more struts.

7. The method of claim 1, wherein upon forming the first and second portions of the body, the body includes a superior endplate surface, an inferior endplate surface, and the opening, the opening configured to receive a fastener and extending from a trailing end of the body through one of the superior and inferior endplate surfaces.

8. The method of claim 1, wherein the body is formed to include surfaces such that movement of the fastener blocker between the first position and the second position is accompanied by tactile feedback.

9. A method of forming an implant, the method comprising the steps of:
depositing and melting successive layers of a first powder material to form a body of the implant, the body including a fastener hole; and
depositing and melting successive layers of a second powder material to form a fastener blocker, the fastener blocker being capable of overlying at least a portion of the fastener hole;
wherein portions of the body and the fastener blocker are formed at the same time and the fastener blocker is captured within the body such that an outer wall of the body covers at least part of a head of the fastener blocker.

10. The method of claim 9, wherein the first powder material is different from the second powder material.

11. The method of claim 9, wherein when the body and the fastener blocker are formed, the fastener blocker is disposed in an internal cavity of the body such that the head of the fastener blocker is irremovable from a trailing end surface of the body, the body being an intervertebral implant.

12. The method of claim 9, wherein the depositing and melting successive layers of the second powder material to form the fastener blocker commences after commencement of the depositing and melting successive layers of the first powder material to form the body and is completed before completion of the depositing and melting successive layers of the first powder material to form the body.

13. The method of claim 9, wherein after the body and the fastener blocker are formed, the fastener blocker is rotatable while captured within the body.

14. The method of claim 13, wherein the body is formed to include surfaces such that rotation of the fastener blocker between a first position and a second position is accompanied by tactile feedback.

15. A method of forming an intervertebral implant using additive layer manufacturing comprising:
alternately depositing and heating successive layers of a first source material to form a first portion of a body of the intervertebral implant;
alternately depositing and heating successive layers of a second source material subsequent to the formation of the first portion to form a fastener blocker; and
alternately depositing and heating successive layers of the first source material subsequent to the formation of the first portion to form a second portion of the body,
wherein subsequent to the formation of the first and second portions, the body includes a leading surface, a trailing surface opposite the leading surface, a superior surface extending between the leading surface and the trailing surface, an inferior surface opposite the superior surface, a first side surface extending between the superior surface and the inferior surface, and a second side surface opposite the first side surface, and
wherein the depositing and heating steps result in the fastener blocker being captured between the first and second portions, the fastener blocker being disposed within the body such that an entirety of the fastener blocker is within a volume defined by the leading surface, the trailing surface, the superior surface, the inferior surface, and the first and second side surfaces, the fastener blocker being spaced apart from the trailing surface.

16. The method of claim 15, wherein the first source material is different from the second source material.

17. The method of claim 15, wherein the fastener blocker is formed to include a head and a shaft, the shaft having a free end surface remote from the head, the free end surface being transverse to a length direction of the shaft and at least partially facing an interior surface of the body.

18. The method of claim 15, wherein the fastener blocker is formed to include a head and a shaft, the head and the shaft being discrete and moveable with respect to one another such that the shaft is removeable from the body and the head is removable from the body when the shaft is removed.

19. The method of claim 15, wherein upon formation of the second portion, the fastener blocker is irremovably enclosed within the body.

20. The method of claim 15, wherein the body is formed to include a fastener-receiving opening extending from the trailing surface to the superior surface or the inferior surface, the fastener-receiving opening being defined in part by a protrusion at the trailing end, the protrusion extending outward from a remainder of the superior surface or the inferior surface.

* * * * *